United States Patent
Artiuch et al.

(10) Patent No.: US 10,760,934 B2
(45) Date of Patent: Sep. 1, 2020

(54) USING LOCALIZED FLOW CHARACTERISTICS ON ELECTRONIC FLOW METER TO QUANTIFY VOLUMETRIC FLOW

(71) Applicant: Natural Gas Solutions North America, LLC, Houston, TX (US)

(72) Inventors: Roman Leon Artiuch, Houston, TX (US); Ertugrul Berkcan, Clifton Park, NY (US); Nannan Chen, Clifton Park, NY (US)

(73) Assignee: Natural Gas Solutions North America, LLC, Houston, TX (US)

( * ) Notice: Subject to any disclaimer, the term of this patent is extended or adjusted under 35 U.S.C. 154(b) by 99 days.

(21) Appl. No.: 15/859,835

(22) Filed: Jan. 2, 2018

(65) Prior Publication Data

US 2018/0143055 A1 May 24, 2018

Related U.S. Application Data

(60) Continuation-in-part of application No. 15/362,582, filed on Nov. 28, 2016, now Pat. No. 10,408,653.
(Continued)

(51) Int. Cl.
*G01F 5/00* (2006.01)
*G01N 33/00* (2006.01)
(Continued)

(52) U.S. Cl.
CPC ............. *G01F 5/00* (2013.01); *G01F 1/3254* (2013.01); *G01F 7/00* (2013.01); *G01F 15/06* (2013.01);
(Continued)

(58) Field of Classification Search
CPC .................. G01F 5/00; G01F 1/3254
(Continued)

(56) References Cited

U.S. PATENT DOCUMENTS

| 3,633,416 A | 1/1972 | Van Dyke et al. |
| 4,290,298 A | 9/1981 | Severson |

(Continued)

FOREIGN PATENT DOCUMENTS

| CN | 201498051 U | 6/2010 |
| CN | 203719723 U | 7/2014 |

(Continued)

OTHER PUBLICATIONS

International Search Report and Written Opinion, dated Apr. 24, 2019, in corresponding PCT/US2018/068081.
(Continued)

*Primary Examiner* — Ricky Ngon
(74) *Attorney, Agent, or Firm* — Paul Frank + Collins P.C.

(57) ABSTRACT

An electronic flow meter that is configured to use localized flow conditions to determine volumetric flow. The embodiments may include a body forming a pass-through channel and a by-pass channel; a semiconductor device comprising a sensor disposed proximate the by-pass channel, the sensor configured to generate a signal with data that reflects localized pressure and localized temperature of a stream in the by-pass channel; and a processing component coupled with the sensor to receive and process the signal so as to identify a flow condition for the stream, select a calculation for volumetric flow rate in response to the flow condition, use data for localized pressure and localized temperature in the calculation to generate a value for the volumetric flow rate; and generate an output with data that reflects the value for the volumetric flow rate.

20 Claims, 9 Drawing Sheets

Related U.S. Application Data which is a division of application No. 14/561,431, filed on Dec. 5, 2014, now abandoned.

(51) Int. Cl.
  *G01F 25/00* (2006.01)
  *G01F 7/00* (2006.01)
  *G01F 1/32* (2006.01)
  *G01M 3/00* (2006.01)
  *G05D 7/00* (2006.01)
  *G01F 15/06* (2006.01)

(52) U.S. Cl.
  CPC ........... *G01F 25/0053* (2013.01); *G01M 3/00* (2013.01); *G01N 33/0006* (2013.01); *G01N 33/0062* (2013.01); *G05D 7/00* (2013.01)

(58) Field of Classification Search
  USPC .......................................... 702/138
  See application file for complete search history.

(56) References Cited

U.S. PATENT DOCUMENTS

| | | | |
|---|---|---|---|
| 4,546,649 A | 10/1985 | Kantor | |
| 4,938,053 A | 7/1990 | Jepson et al. | |
| 5,029,470 A | 7/1991 | Gamperl | |
| 5,080,131 A | 1/1992 | Ono et al. | |
| 5,159,951 A | 11/1992 | Ono et al. | |
| 5,249,462 A | 10/1993 | Bonne | |
| 5,861,561 A | 1/1999 | Van Cleve et al. | |
| 5,864,067 A | 1/1999 | Ligneul et al. | |
| 7,212,953 B1 | 5/2007 | Artiuch | |
| 7,866,208 B1 | 1/2011 | Ueda et al. | |
| 8,342,018 B2 | 1/2013 | Huang et al. | |
| 8,418,549 B2 | 4/2013 | Speldrich et al. | |
| 8,966,970 B2 | 3/2015 | Berkcan et al. | |
| 9,032,790 B2 | 5/2015 | Braun et al. | |
| 2003/0236638 A1* | 12/2003 | Shajii ................... G01F 1/6847 702/45 |
| 2007/0084286 A1 | 4/2007 | Ajay et al. | |
| 2007/0099527 A1 | 5/2007 | Brun et al. | |
| 2007/0112536 A1 | 5/2007 | Artiuch et al. | |
| 2008/0066527 A1 | 3/2008 | Ajay | |
| 2009/0187356 A1 | 7/2009 | Artiuch | |
| 2010/0030388 A1* | 2/2010 | Wang ..................... G01F 1/363 700/282 |
| 2011/0061469 A1 | 3/2011 | Maahs | |
| 2011/0166800 A1 | 7/2011 | Berkcan et al. | |
| 2011/0303019 A1 | 12/2011 | Gysling | |
| 2012/0125337 A1 | 5/2012 | Asanoi | |
| 2012/0174650 A1 | 7/2012 | Ariessohn et al. | |
| 2013/0079667 A1* | 3/2013 | Berkcan ................. A61B 5/087 600/586 |
| 2014/0165718 A1* | 6/2014 | Berkcan ................. G01F 1/6842 73/204.21 |
| 2014/0260667 A1 | 9/2014 | Berkcan et al. | |
| 2016/0161307 A1* | 6/2016 | Berkcan ............. G01N 33/0062 73/861.08 |
| 2017/0038237 A1* | 2/2017 | Chen ..................... E21B 43/34 |
| 2017/0328753 A1* | 11/2017 | Briese ................... G01F 1/6842 |

FOREIGN PATENT DOCUMENTS

| | | |
|---|---|---|
| CN | 204314987 U | 5/2015 |
| EP | 2312276 A1 | 4/2011 |
| JP | 08005416 A | 1/1996 |
| JP | 2001241979 A | 9/2001 |
| JP | 2003075214 A | 3/2003 |
| JP | 2003075214 JP | 3/2003 |
| JP | 2003149016 A | 5/2003 |
| WO | 9502812 A1 | 1/1995 |
| WO | 2014099810 A1 | 6/2014 |
| WO | 2014151003 A2 | 9/2014 |

OTHER PUBLICATIONS

First Office Action dated Oct. 7, 2019, issued by the Japanese Patent Office in corresponding JP2015-234385.

* cited by examiner

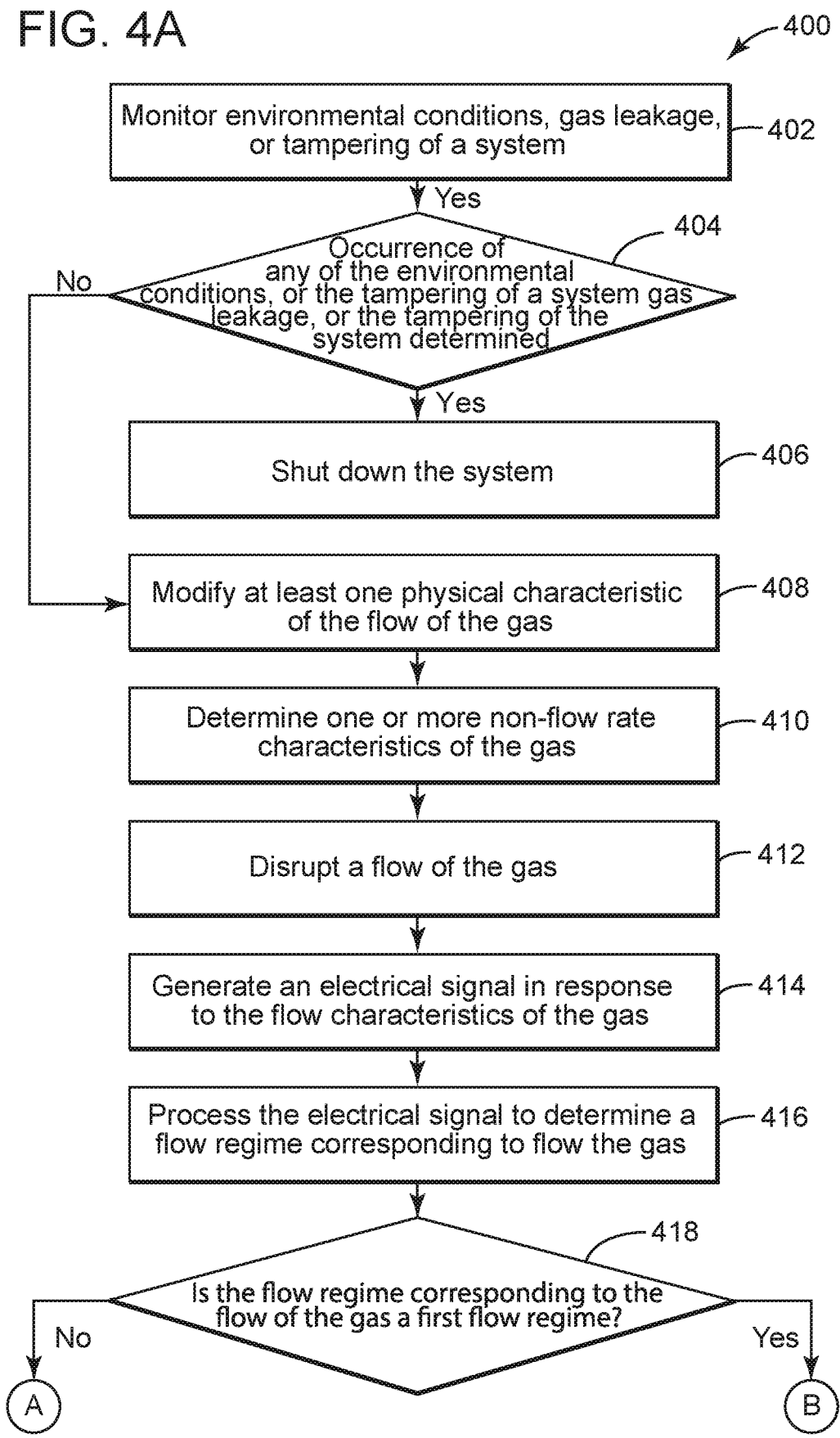

USING LOCALIZED FLOW CHARACTERISTICS ON ELECTRONIC FLOW METER TO QUANTIFY VOLUMETRIC FLOW

CROSS-REFERENCE TO RELATED APPLICATIONS

This application is a continuation-in-part of U.S. patent application Ser. No. 15/362,582, filed on Nov. 28, 2016, and entitled "SYSTEM AND METHOD FOR METERING GAS BASED ON AMPLITUDE AND/OR TEMPORAL CHARACTERISTICS OF AN ELECTRICAL SIGNAL," which is a divisional of U.S. patent application Ser. No. 14/561,431, filed on Dec. 5, 2014, and entitled "SYSTEM AND METHOD FOR METERING GAS." The content of these applications is incorporated herein by reference in its entirety.

BACKGROUND

Metrology hardware finds use across a wide range of applications. For example, the fuel gas industry uses metering systems, or "flow meters," to measure consumption, bill customers, and manage inventory. Some of these flow meters are mechanical, positive-displacement devices. Rotary-types of these devices may include an impeller that rotates in response to flow of gas. In other types, the flow of gas translates a diaphragm or bellows. Other mechanical devices may leverage a turbine or like rotating element (e.g., a pinwheel).

Advances in technology may eclipse these mechanically-based flow meters. This technology makes possible use of electronic hardware to evaluate parameters of the flowing material to appropriately quantify, for example, volumetric flow that forms the foundation for customer billing. However, for electronic flow meters to substitute for mechanically-based flow meters, these devices often must satisfy certain "legal metrology" standards that regulatory bodies promulgate under authority or legal framework of a given country or territory. These standards may be in place to protect public interests, for example, to provide consumer protections for metering and billing use of fuel. These protections may set definitions for units of measure, realization of these units of measure in practice, application of traceability for linking measurement of the units made in practice to the standards and, importantly, ensure accuracy of measurements.

SUMMARY

The subject matter of this disclosure relates to electronic flow meters and related metrology hardware. Of particular interest herein are improvements that configure electronic flow meters to accurately quantify volume of gas (or "material") flow. Some embodiments comprise a sensor that can generate data for a sample stream of the flowing material. This data may reflect flow conditions including localized "measured" conditions, like measured pressure and measured temperature at or proximate the sensor. At low flow, the embodiments may use the data from the sensor to calculate standardized volumetric flow of the sample. Data on measured pressure is advantageous for the device to account in real-time for density of the sample (proximate the sensor), which the embodiments need to accurately convert standardized volumetric flow to volumetric flow of the flowing material at these low flow conditions. At higher flow, the embodiments may also use the data to arrive at the volumetric flow. But the embodiments will benefit from values for measured pressure and measured temperature at these higher flow conditions and, more generally, across all flow conditions, because the device can use the data to apply a "correction" to any calculated volumetric flow. This correction, in turn, configures the values for volumetric flow to properly reflect ambient conditions proximate the electronic flow meter.

In this regard, this disclosure may refer to the volume of gas flow in several forms. "Actual" volumetric flow rate refers to the volume of gas flowing in the meter at prevailing temperature and pressure. "Standard" volumetric flow rate (or "standard" flow rate) refers to the equivalent volumetric flow rate of gas that would be moving through the meter had the temperature and pressure been at standard or "reference" condition for temperature and pressure. Calculations to convert actual volumetric flow rate to standard volumetric flow rate may accord with the Ideal Gas Law as shown in Equation (1) below, $$V_r = \left(\frac{P_m}{P_r}\right) \times \left(\frac{T_r}{T_m}\right) \times V_m, \qquad \text{Equation (1)}$$

where $V_r$ is standard volumetric flow at reference conditions, $V_m$ is actual volumetric flow at prevailing conditions, $P_m$ is the prevailing pressure, $P_r$ is the reference pressure, $T_m$ is the prevailing temperature, and $T_r$ is the reference temperature. The disclosure may also identify standard volumetric flow rate $V_r$ as "corrected" volumetric flow rate (at the reference conditions), as well. This disclosure also contemplates that standard volumetric flow rate may relate to the mass flow rate of gas by a multiplicative constant that depends on the density of the gas at the reference conditions. Volumetric flow rate or actual volumetric flow rate may also be reported in, but not limited to, standard volumetric flow rate, corrected volumetric flow rate, and mass flow rate. It follows then that embodiments may convert data from sensors (for example, sensors that measure conditions like temperature and pressure) to forms including, but not limited to, these forms of flow rates as well. The embodiments may also obtain flow parameters from the data generated by these sensors and one or both of an amplitude characteristic of the data and a temporal characteristic of the data. The embodiments may convert the data and the flow parameters to volumetric flow rate by different processes in the various flow regimes that are relevant, as detailed in the sequel.

DRAWINGS

Reference is now made briefly to the accompanying figures, in which:

FIGS. 4A and 4B depict a flow chart illustrating an example method for metering gas, in accordance with aspects of the present specification;

Figure 1:
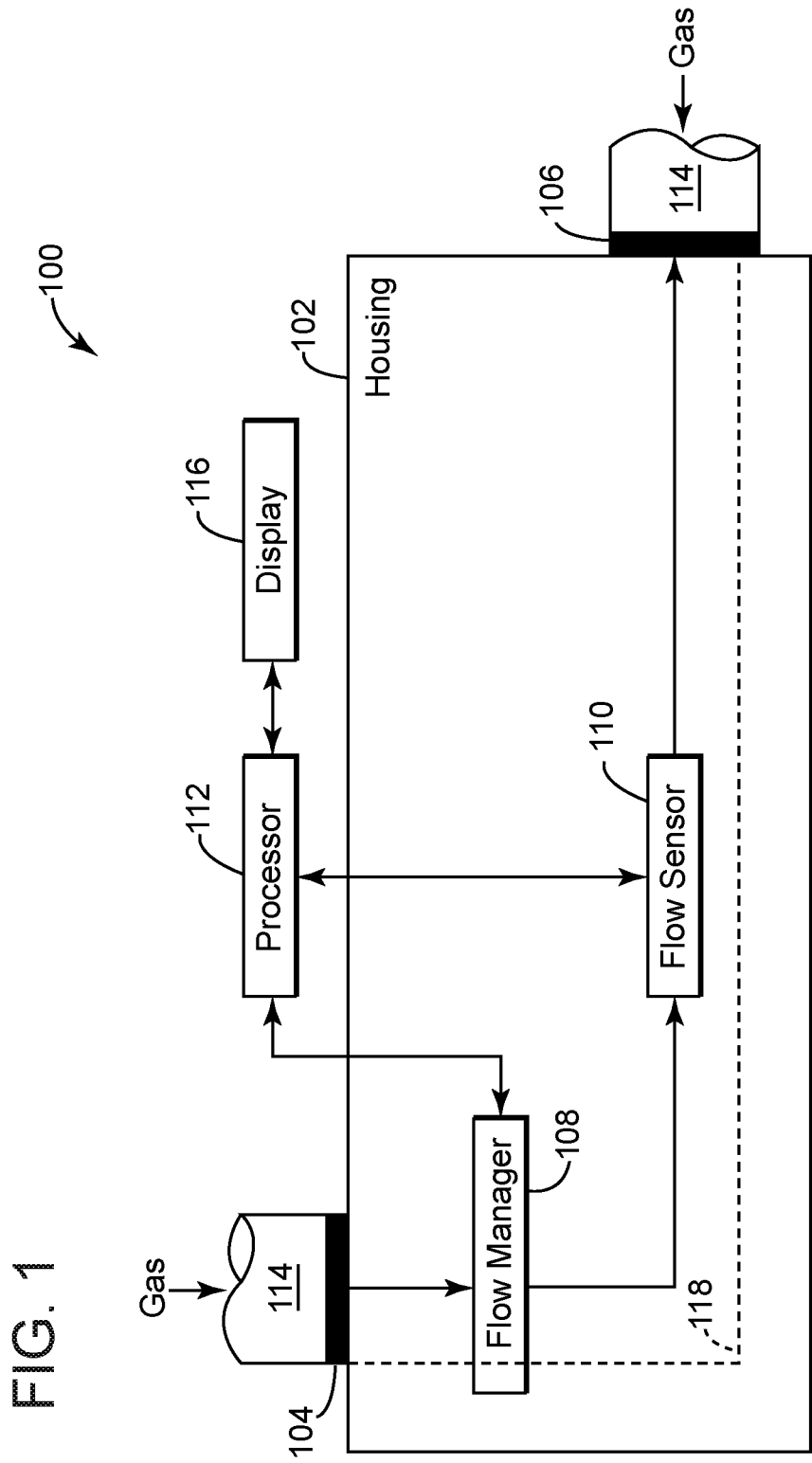
FIG. 1 is a diagrammatical illustration of a system for metering gas, in accordance with aspects of the present specification.

Where applicable like reference characters designate identical or corresponding components and units throughout the several views, which are not to scale unless otherwise indicated. The embodiments disclosed herein may include elements that appear in one or more of the several views or in combinations of the several views. Moreover, methods are exemplary only and may be modified by, for example, reordering, adding, removing, and/or altering the individual stages.

DETAILED DESCRIPTION

The specification may be best understood with reference to the detailed figures and description set forth herein. Various embodiments are described hereinafter with reference to the figures. However, those skilled in the art will readily appreciate that the detailed description given herein with respect to these figures is for explanatory purposes as the method and the system extend beyond the described embodiments.

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the terms "may" and "may be" indicate a possibility of an occurrence within a set of circumstances, a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable.

FIG. 1 is a diagrammatical illustration of a system 100 for metering gas, in accordance with aspects of the present specification. The system 100 includes a housing 102 having an input port 104 and an output port 106. In addition, the system 100 includes a flow manager 108, a flow sensor 110, and a processor 112. Optionally, the system 100 may also include a display 116. The flow manager 108 and the flow sensor 110 may be disposed within the housing 102. The processor 112 may be disposed on a printed circuit board (PCB) (not shown). In one embodiment, the PCB may be disposed on or about the housing 102. Moreover, the system 100 may also include an energy source such as a battery (not shown) coupled to the flow manager 108, the flow sensor 110, and the processor 112. The energy source may supply energy to the flow manager 108, the flow sensor 110, and the processor 112. In one embodiment, the flow manager 108 may be disposed in the proximity of the input port 104. In another embodiment, the flow manager 108 may be disposed in the proximity of the output port 106.

The system 100 may be operatively coupled to a pipeline 114 as shown in FIG. 1 and configured to meter a gas flowing through the pipeline 114. More particularly, the system 100 may be operatively coupled to the pipeline 114 such that the gas flowing through the pipeline 114 is received at the input port 104. Moreover, the housing 102 and the output port 106 may be arranged such that the gas is discharged from the output port 106. In one embodiment, a flow path of at least a portion of the gas flowing in the housing 102 may be indicated by a dashed line 118. The pipeline 114 may be a part of a household or an industrial setup for supplying gas, such as a natural gas. In one embodiment, the input port 104 and the output port 106 may form an integral part of a body of the housing 102. In some other embodiments, the input port 104 and the output port 106 may be operatively coupled to the housing 102. As noted hereinabove, the system 100 may be configured to meter the gas flowing through the pipeline 114. The term 'meter' as used herein may be used to refer to determining one or more flow parameters of the gas including, but not limited to, a mass flow rate, an accumulated volume of the gas, a volumetric flow rate, a cumulative gas volume per a determined time unit, or combinations thereof.

The housing 102 may be configured to receive the gas from the input port 104. In addition, the housing 102 may further be configured to allow a flow of the gas from the input port 104 to the output port 106. As previously noted, the flow manager 108 and/or the flow sensor 110 may be disposed within the housing 102. More particularly, in one embodiment, the flow manager 108 and/or the flow sensor 110 may be arranged in the housing 102 such that the flow manager 108 and/or the flow sensor 110 are in the flow path 118 of at least a portion of the gas flowing from the input port 104 to the output port 106.

As will be appreciated, various physical characteristics associated with the flow of the gas flowing in the system 100 including, but not limited to, a separability of the flow of the gas, a pressure of the gas, a temperature of the gas, and a level of impurities in the gas affect the measurement results. Accordingly, it may be desirable to account for one or more of these physical characteristics while metering the gas. In accordance with the aspects of the present specification, the flow manager 108 is configured to modify at least one physical characteristic of the flow of the gas in the housing 102 in order to minimize the effect of the one or more of the physical characteristics on the measurement determined by the system 100. In one embodiment, there may be flow modifier configured to modify at least on physical characteristic of the stream in the by-pass channel. Examples of such flow modifiers may include bluff objects, flow regulators, flow straighteners, flow restrictors, etc.

The term "separability of the flow of the gas" as used herein may be used to refer to an ability to cause a separation of the flow of the gas in a vicinity of a surface such as a surface of the housing 102 where the effect of viscosity of the gas may be significant. Typically, in fluid mechanics, a boundary layer is a layer of fluid (e.g., the gas) in the vicinity of a bounding surface such as the surface of the housing 102 where the effect of the viscosity of the gas may be significant. As will be appreciated, the separation of the flow of the gas occurs when the boundary layer travels far enough against a pressure gradient that a speed of the boundary layer relative to the object (e.g., the surface of the housing 102) becomes substantially close to zero. Consequently, the separation of the gas flow may lead to formation of eddies and vortices. By way of example, the separability of the flow of the gas may be related to the lack of laminarity of the flow of the gas. More particularly, the separability of the flow of the gas may result in the separation of the boundary layer such as a laminar boundary layer.

In one embodiment, at least a portion of the gas flows by the flow manager 108. Moreover, a portion of the gas in the housing 102 may also flow through the flow sensor 110. The flow sensor 110 may be configured to generate an electrical signal such as a voltage signal or a current signal in response to the flow characteristics of the gas in the housing 102. The term 'electrical signal' is hereinafter also referred to as a signal. Some examples of the flow sensor 110 include, but are not limited to, a calorimetric flow sensor, a hot wire anemometer, a mass flow rate sensor, a volumetric flow rate sensor, a pressure sensor, a temperature sensor, or combinations thereof. Moreover, the flow sensor 110 may also include one or more sensing elements (not shown in FIG. 1). Examples of the sensing elements may include, but are not limited to, micro-electromechanical flow sensing elements, thermopiles, temperature sensing elements, pressure sensing elements, or combinations thereof. The electrical signal generated by the flow sensor 110 may have an amplitude characteristic and a temporal characteristic. The amplitude characteristic may include, but is not limited to, a magnitude, a scale, a breadth, or combinations thereof. Similarly, the temporal characteristic may include, but is not limited to, a period, a frequency, a zero crossing rate, a phase, a time-resolved demodulation, a frequency-resolved demodulation of the signal, or combinations thereof. As noted more below, these characteristics are useful to identify flow conditions of the stream. In one implementation, the signal may have an oscillatory characteristics or non-oscillatory characteristic, which may also benefit the process to identify flow conditions. Such "oscillation" may be present in the form of vorticies, Karman vortex streets, or oscillations due to Coanda effect, some of which are used in oscillatory sensors. The frequency of oscillation may be picked up and contributed to the sensor signal, and so may help to form the basis for volumetric flow measurement.

Furthermore, the processor 112 is operatively coupled to the flow manager 108 and the flow sensor 110. In one embodiment, the processor 112 may be configured to control the functionality of the flow manager 108 to aid in the modification of the physical characteristics of the flow of the gas in the housing 102. More particularly, the processor 112 may be configured to control the flow manager 108 to allow the flow manager 108 to modify one or more physical characteristics of the gas in the housing 102. It may be noted that it may be desirable to maintain the values of the one or more physical characteristics within corresponding desirable ranges of values. In one embodiment, the desired ranges of values of the one or more physical characteristics may be stored in memory (not shown) associated with the processor 112.

In another embodiment, the processor 112 may be configured to receive the electrical signal generated by the flow sensor 110. Furthermore, the processor 112 may also be configured to determine at least one flow parameter of the gas based on the electrical signal received from the flow sensor 110. Some examples of the flow parameter include, but are not limited to, the mass flow rate of the gas, the accumulated volume of the gas, the volumetric flow rate of the gas, the cumulative gas volume per the determined time unit, or combinations thereof. More particularly, the processor 112 is configured to determine the flow parameter based on the amplitude characteristic, the temporal characteristic, or both the amplitude characteristic and the temporal characteristic of the electrical signal.

In one example, the processor 112 may be a signal processor. In this embodiment, the processor 112 may be configured to perform a spectral analysis of the electrical signal received from the flow sensor 110. Some examples of signal processing techniques that may be implemented by the processor 112 to perform the spectral analysis may include, but are not limited to, a Fast Fourier Transform (FFT), the heterodyne principle, a phase-locked loop, or combinations thereof.

Additionally, in certain embodiments, the system 100 may include the display 116. In one embodiment, the values of the flow parameter determined by the processor 112 may be visualized on the display 116. By way of example, the display 116 may include a light emitting diode (LED) display, a liquid crystal display (LCD), and the like. In one embodiment, the display 116 may be disposed on the housing 102. However, in certain embodiments, the display 116 may be disposed at a remote location. The display 116 may be communicatively coupled to the processor 112. In one embodiment, the display 116 may be coupled to the processor 112 via a wired medium. In such an instance, serial or parallel communication protocols may be implemented to aid in the data communication between the processor 112 and the display 116.

In another embodiment, the display 116 may be coupled to the processor 112 via a wireless communication link. In such a configuration, the system 100 may further include a wireless communication unit (not shown) to aid in the data communication between the processor 112 and the display 116 over the wireless communication link. By way of example, the wireless communication unit may use wireless communication protocols such as Bluetooth or Wi-Fi. In certain embodiments when the display 116 is disposed at the remote location, the wireless communication unit may use wireless communication protocols such as Wi-Max and/or cellular communication protocols such as 2G, 3G, or 4G.

In yet another embodiment, an additional display may be provided at the remote location in addition to the display 116 disposed on the housing 102. The additional display may be coupled to the processor 112 via a wireless communication link. The wireless communication unit may aid in the data communication between the processor 112 and the remotely disposed display over the wireless communication link.

Implementing the system 100 for metering gas a described with respect to FIG. 1 aids in determining flow parameters such as the mass flow rate of the gas, the accumulated volume of the gas, the volumetric flow rate of the gas, the cumulative gas volume per the determined time unit, or combinations thereof. Moreover, the flow parameters thus determined may not be impacted by gas density fluctuations, moisture fluctuations, gas mixture fluctuations, and the like.

Figure 2:
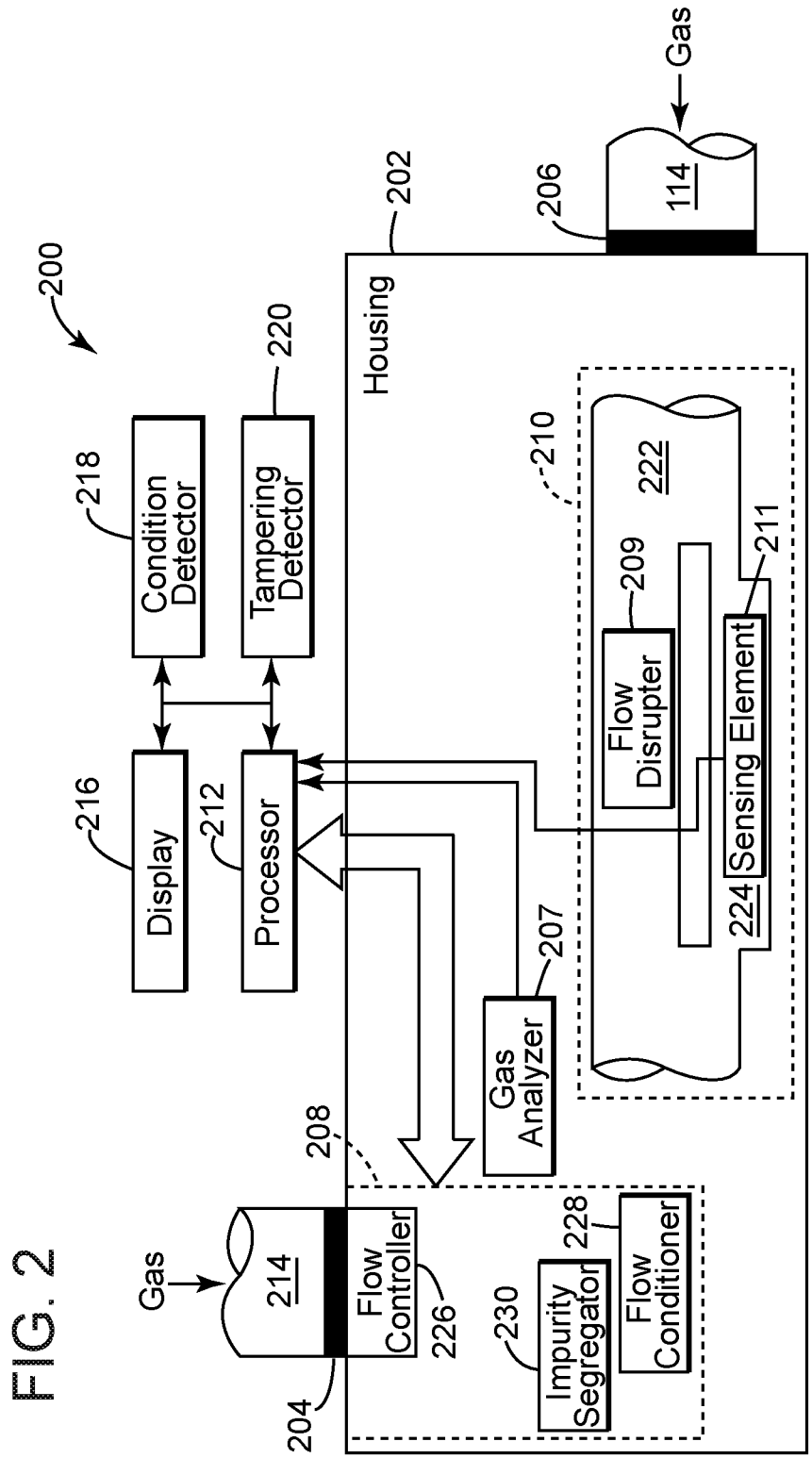
FIG. 2 is a diagrammatical illustration of another system for metering gas, in accordance with aspects of the present specification.

FIG. 2 is a diagrammatical illustration of another embodiment of system 200 for metering gas, in accordance with aspects of the present specification. FIG. 2 is discussed in conjunction with the elements of FIG. 1. The system 200 includes a housing 202 having an input port 204 and an output port 206. In a presently contemplated configuration, the system 200 may further include a flow manager 208, a gas analyzer 207, a flow sensor 210, a processor 212, a condition detector 218, and a tampering detector 220. The system 200 may also include a display 216. Moreover, the system 200 may also include an energy source such as a battery (not shown) and a wireless communication unit (not shown). The energy source may supply energy to the flow manager 208, the gas analyzer 207, the flow sensor 210, the processor 212, the condition detector 218, and the tampering detector 220. The wireless communication unit may be coupled to the processor 212. It may be noted that the arrangement and/or the functionality of the housing 202, the input port 204, the output port 206, the flow manager 208, the flow sensor 210, the processor 212, a pipeline 214, the display 216, the energy source, and the wireless communication unit may be similar to the corresponding elements of FIG. 1.

In one embodiment, the system 200 may be operatively coupled to the pipeline 214 and configured for metering the gas flowing through the pipeline 214. By way of example, in the embodiment of FIG. 2, the system 200 is configured to determine a flow parameter such as a volumetric flow rate of the gas flowing through the pipeline 214. The system 200 may also be configured to determine other flow parameters including, but not limited to, a mass flow rate of the gas, an accumulated volume of the gas, a cumulative gas volume per a determined time unit, or combinations thereof.

In one embodiment, the flow manager 208 may be arranged in the housing 202. The flow manager 208 is configured to modify the at least one physical characteristic of the flow of the gas in the housing 202. In one example embodiment, the flow manager 208 may include a flow controller 226, a flow conditioner 228, and an impurity segregator 230.

The flow controller 226 may include a shut-off valve (not shown) configured to selectively stop the flow of the gas from the input port 204 to the output port 206, or vice-versa. In one embodiment, the shut-off valve may be disposed in the proximity of the input port 204. In another embodiment, the shut-off valve may be disposed in the proximity of the output port 206. Moreover, the flow conditioner 228 may be configured to control a separability of the flow of the gas in the housing 202. The control of the separability of the flow of the gas may include reducing turbulences, swirls, and/or asymmetric flow profiles in the flow of the gas.

The impurity segregator 230 may be configured to remove impurities from the gas flowing through the housing 202. The impurities in the gas, such as natural gas, may include, but are not limited to, one or more of dust, foreign objects, glycol, hydrogen sulfide ($H_2S$), sulfur dioxide ($SO_2$), methyl mercaptan ($CH_4S$), carbonyl sulfide (OCS), carbon disulfide ($CS_2$), nitrogen, carbon dioxide ($CO_2$), water vapor, and combinations thereof. Various examples of the impurity segregator 230 may include, but are not limited to, a magnetic dust trap, a cyclone type dust segregator, charcoal, activated carbon, monoethlamine (MEA) solution, a bed of iron filings, and the like. In one embodiment, the impurity segregator 230 may be disposed proximate to an internal surface of the housing 102. More particularly, the impurity segregator 230 may be disposed proximate to any corner of the housing 202. In such a configuration, the impurities removed by the impurity segregator 230 may be deposited about the corner of the housing 202. However, in certain embodiments, the impurity segregator 230 may be positioned at other locations within the housing 202.

Further, in certain embodiments, the gas analyzer 207 may also be disposed in the housing 202. In one embodiment, the gas analyzer 207 may be disposed such that the gas analyzer 207 is aligned with one or more elements of the flow manager 208. In other embodiments, the gas analyzer 207 may be disposed at other locations within the housing 202. The gas analyzer 207 is configured to determine one or more non-flow rate characteristics of the gas. In one example, the non-flow rate characteristics of the gas may include characteristics such as, but not limited to, a gas density, a gas mixture and composition, a gas temperature, a gas pressure, humidity, an energy content of the gas, levels of various impurities contained in the gas, or combinations thereof. Furthermore, the gas analyzer 207 may include one or more sensors that aid in the determination of constituents of the gas, temperature, pressure, and caloric value (indicative of the energy content) of the gas, and/or levels of various impurities in the gas flowing through the housing 202. The gas analyzer 207 may also be configured to communicate the determined values of the non-flow rate characteristics to the processor 212.

Moreover, the flow sensor 210 is also disposed in the housing 202. Some examples of the flow sensor 210 include, but are not limited to, a calorimetric flow sensor, a hot wire anemometer, a mass flow rate sensor, a volumetric flow rate sensor, a pressure sensor, a temperature sensor, or combinations thereof. For the purpose of simplicity of illustration, in one example of FIG. 2, the flow sensor 210 is described as functionally combining functions of the mass flow rate sensor and the volumetric flow rate sensor. In one embodiment of the present specification, the flow sensor 210 may include one or more of a flow conduit 222, a bypass channel 224, a flow disrupter 209, and one or more sensing elements such as a sensing element 211. The flow conduit 222 may be configured to allow therethrough, at least a portion of the flow of the gas flowing in the housing 202.

Moreover, in one embodiment, the flow disrupter 209 may be disposed in the flow conduit 222, as depicted in FIG. 2. Although in the embodiment of FIG. 2, the flow disrupter 209 is shown to be a part of the flow sensor 210, use of the flow disrupter 209 with the flow manager 208 and/or the gas analyzer 207 is also contemplated. In an instance when the flow disrupter 209 is disposed within the gas analyzer 207, the flow disrupter may aid in the determination of the non-flow rate characteristics of the gas. In certain embodiments, the flow disrupter 209 may be disposed outside the flow sensor 210 in the housing 202.

The flow disrupter 209 may be configured to impart disturbances to the flow of the gas in the housing 202 and/or the flow conduit 222. The disturbances produced in the flow of the gas may be in the form of vortices, pressure, and/or velocity fluctuations. The flow disrupter 209 may have shapes including, but not limited to, an active actuator, a blunt flow disrupter, a planar flow disrupter, a rectangular flow disrupter, and combinations thereof.

The bypass channel 224 may be in fluid communication with the flow conduit 222. More particularly, as depicted in FIG. 2, in one embodiment, the bypass channel 224 may be positioned such that the bypass channel 224 is disposed external to the flow conduit 222. In other embodiments, the bypass channel 224 may be disposed within the flow conduit 222.

In one example embodiment, the flow conduit 222, the bypass channel 224, the flow disrupter 209, and/or the sensing element 211 may be configured to have a geometrical relationship. Some example parameters that may be used to determine the geometrical relationship between the bypass channel 224, the flow conduit 222, the flow disrupter 209, and the sensing element 211 may include, but are not limited to, respective dimensions of the bypass channel 224, the flow conduit 222, and the flow disrupter 209, positioning of the flow disrupter 209 in the flow conduit 222 relative to the bypass channel 224 and/or the sensing element 211, the dimensions of the flow disrupter 209 with respect to the dimensions of the flow conduit 222, or combinations thereof. Furthermore, the geometrical relationship between the flow conduit 222, the bypass channel 224, the flow disrupter 209, and/or the sensing element 211 may be selected such that the geometrical relationship aids in establishing a phase difference between a pressure of the gas flow at the input of the bypass channel 224 and a pressure of the gas flow at the output of the bypass channel 224. Furthermore, a value of this phase difference may be selected such that the phase difference results in an increase in a signal-to-noise ratio of an electrical signal generated by the sensing element 211. By way of example, the phase difference may be selected such that the flow pressure at the input of the bypass channel 224 and the flow pressure at the output of the bypass channel 224 are substantially out-of-phase relative to one another. Such a phase difference may aid in effectively suppressing common mode noise effects in the electrical signal generated by the sensing element 211.

In one embodiment, the bypass channel 224 and the flow disrupter 209 are arranged in the flow conduit 222 such that at least some flow characteristics of the gas flowing in the bypass channel 224 are affected. By way of example, the bypass channel 224 and the flow disrupter 209 may be positioned such that the flow rate of the gas flowing in the bypass channel 224 is altered. More particularly, in one embodiment, the flow conduit 222, the bypass channel 224, and the flow disrupter 209 may be dimensioned and arranged such that when the flow rate of the gas flowing through the flow conduit 222 is low (laminar flow) no disturbance is imparted to the flow of the gas in the flow conduit 222. Consequently, no vortices are formed in the flow conduit 222 when the flow of the gas is laminar. A range of such low flow rates for which the vortices are not formed in the flow conduit 222 may generally be referred to as a first flow regime.

In another embodiment, the flow conduit 222, the bypass channel 224, and the flow disrupter 209 may be dimensioned and arranged such that when the flow rate of the gas flowing through the flow conduit 222 is high, disturbances may be imparted to the flow of the gas by the flow disrupter 209. Consequently, vortices are formed in the gas flowing in the flow conduit 222 when the flow rate of the gas is high. The term "second flow regime" may be used to refer to a range of such high flow rates that result in the formation of the vortices in the gas flowing in the flow conduit 222. In the second flow regime, the vortices may be formed such that the temporal characteristic, for example, the frequency ($V_f$) of the vortices is proportional to the volumetric flow rate of the gas flowing through the flow conduit 222.

Furthermore, in one embodiment, the sensing element 211 may be disposed in the bypass channel 224. In another embodiment, the sensing element 211 may be disposed in the flow conduit 222. Examples of the sensing element 211 may include, but are not limited to, micro-electromechanical flow sensing element, a thermopile, a temperature sensing element, a pressure sensing element. In one embodiment, the thermopile, temperature sensing element, and pressure sensing element may include one or more micro-electromechanical sensing (MEMS) elements. The disturbances imparted by the flow disrupter 209 in the second flow regime may cause oscillatory pressure fluctuations at the input and/or output of the bypass channel 224. Such oscillatory pressure fluctuations may in turn cause a measurable frequency modulation of the flow of the gas flowing through the bypass channel 224. It may be noted that flow rates corresponding to the first flow regime may result in a substantially steady pressure at the input and output of the bypass channel 224 or a steady flow in the bypass channel 224.

As previously noted, the sensing element 211 of the flow sensor 210 is configured to generate the electrical signal in response to the flow characteristics of the gas flowing in the housing 202. For example, the electrical signal may be a voltage (V) signal or a current (I) signal. Accordingly, in the second flow regime where the vortices are formed in the gas flowing through the flow conduit 222, the sensing element 211 may generate an alternating current (AC) voltage signal. The frequency ($V_f$) of the AC voltage signal thus generated is proportional to or directly related to a volumetric flow rate (e.g., liter/second) of the gas flowing through the housing 202. For ease of explanation, a parameter such as the frequency ($V_f$) is used to represent temporal characteristics of the AC voltage signal. However, embodiments of the present specification are also applicable to other temporal characteristics of the AC voltage signal. In one embodiment, the generated AC voltage signal may be at an offset from a zero value. Accordingly, the AC voltage signal thus generated may also have a direct current (DC) value.

However, in the first flow regime where no vortices are formed, the sensing element 211 of the flow sensor 210 may generate a DC voltage having a magnitude ($V_{amp}$) which is related to a mass flow rate (e.g., kilogram/second) of the gas flowing through the housing 202. As will be appreciated, the volumetric flow rate of the gas may be determined based at least on the density of the gas. Also, as noted previously, the density of the gas may vary substantially depending on various factors associated with the gas, such as the pressure, temperature, gas composition, or combinations thereof. Hence, in the first flow regime, the mass flow rate of the gas may not be a clear indicator of the volumetric flow rate of the gas. Consequently, determining the volumetric flow rate based on the mass flow rate may be laborious task.

Figure 3:
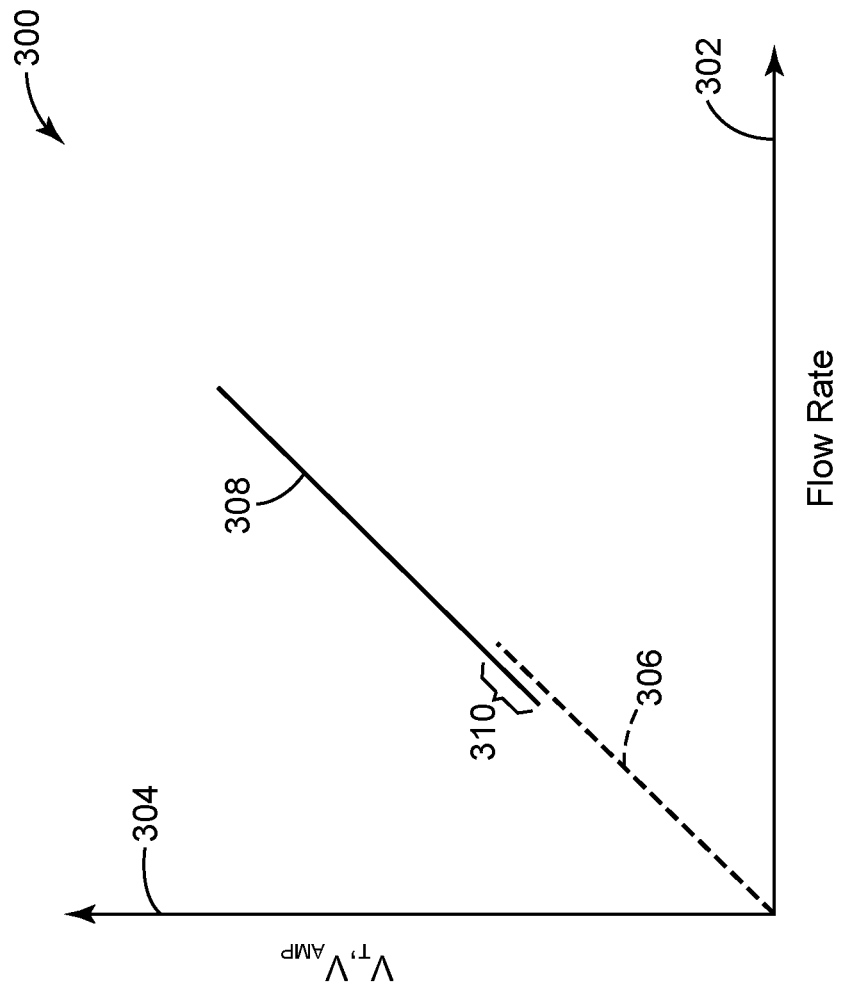
FIG. 3 is a graphical illustration depicting a response of a sensor in different flow regimes, in accordance with aspects of the present specification.

FIG. 3 is a graphical illustration 300 depicting a response of a sensor such as the flow sensor 210 of FIG. 2 in different flow regimes, in accordance with aspects of the present specification. FIG. 3 is explained in conjunction with the elements of FIG. 2. The X-axis 302 of the graphical illustration 300 represents a flow rate and the Y-axis 304 represents a magnitude ($V_{amp}$) and a frequency ($V_f$) of a voltage signal generated by the sensing element 211 of the flow sensor 210. The magnitude ($V_{amp}$) and the frequency ($V_f$) of the voltage signal generated by the flow sensor 210 may be referred to as a sensor response. As depicted in the graphical illustration 300, a first flow regime may be represented by a curve 306 and a second flow regime may be represented by a curve 308. It may be noted that in FIG. 3, the curves 306 and 308 are illustrated as straight lines for purposes of simplicity of illustration and should not be interpreted as an indication of a linear relationship between the flow rate 302 and the sensor response 304.

Also, reference numeral 310 is used to represent a flow regime, hereinafter referred to as a third flow regime, where the first flow regime 306 and the second flow regime 308 overlap. As depicted in FIG. 3, the third flow regime 310 is located near a lower end of the second flow regime 308. Therefore, in the third flow regime 310, vortices may be formed in the gas flowing in the flow conduit 222. Consequent to the formation of the vortices in the gas in the third flow regime 310, an AC voltage signal may be generated by the sensing element 211 of the flow sensor 210. However, the third flow regime 310 is also proximate to the first flow regime 306, thereby allowing measurement of an amplitude characteristic such as a magnitude ($V_{amp}$) of the voltage signal generated by the sensing element 211. Accordingly, the third flow regime 310 may be characterized by a range of flow rates in which both the temporal and amplitude characteristics of the voltage signal generated by the flow sensor 210 are measurable. In one embodiment, a parameter such as the magnitude ($V_{amp}$) of the voltage signal is used to represent amplitude characteristics of the voltage signal for the purpose of simplicity of the description. However, embodiments of the present specification are also applicable to other amplitude characteristics listed hereinabove.

Referring again to FIG. 2, characteristics of the third flow regime 310 (see FIG. 3) may be utilized to develop a calibration function. In one embodiment, the calibration function may be developed during a learning phase of the system 200. In another embodiment, the calibration function may be developed when the system 200 is operating to meter the gas. In yet another embodiment, the calibration function that is developed during the learning phase may be updated (continuously or at regular intervals of time) when the system 200 is operating to meter the gas. This dynamic updating of the calibration function when the system 200 is in operation may be referred to as an automatic recalibration of the system 200.

As will be appreciated due to the presence of the vortices in the second flow regime allows measurement of a volumetric flow rate of the gas in the housing 202. However, in the first flow regime, it may not be feasible to determine the volumetric flow rate due to the absence of vortices in the gas. In accordance with one aspect of the present specification, the system 200 may be configured to determine the calibration function to allow the system 200 to obtain the volumetric flow rate in the first flow regime. The calibration function represents a relationship between the volumetric flow rate determined based on the frequency ($V_f$) of the voltage signal and the mass flow rate determined based on the magnitude ($V_{amp}$) of the voltage signal in the third flow regime.

In one embodiment, during the learning phase, the system 200 may be configured to determine both the volumetric flow rate of the gas and the mass flow rate the gas for different flow rates in the third flow regime. For example, in the learning phase, the gas having a flow rate corresponding to the third flow regime is passed through the housing 202. The processor 212 may be configured to determine both the volumetric flow rate and the mass flow rate based on the frequency ($V_f$) and the magnitude ($V_{amp}$), respectively, of the voltage signal generated by the sensing element 211. In one embodiment, during the learning phase, the processor 212 may also be configured to obtain the values of the non-flow rate characteristics of the gas from the gas analyzer 207 while determining the volumetric flow rate and the mass flow rate. As previously noted, some examples of the non-flow rate characteristics of the gas may include one or more of the constituents of the gas, temperature, pressure, and caloric value of the gas, and/or levels of various impurities contained in the gas. This process may be repeated for different values of the flow rates corresponding to the third flow regime. The processor 212 may be configured to develop a calibration function based on the values of the volumetric flow rates, the mass flow rates, and one or more of the non-flow rate characteristics of the gas that correspond to the different flow rates associated with the third flow regime.

Once the calibration function is determined by the system 200 during the learning phase, the system 200 may be operatively coupled to the pipeline 214. As will be appreciated, vortices may or may not be formed in the fluid conduit 222 depending on the flow rate of the gas in the pipeline 214. In one embodiment, if the flow rate of the gas allows the formation of vortices in the gas (e.g., in the second flow regime), the AC voltage signal is generated by the sensing element 211. The processor 212 may be configured to determine a flow parameter such as the volumetric flow rate of the gas based on the frequency ($V_f$) of the AC voltage signal generated by the sensing element 211. In one embodiment, the processor 212 may utilize spectral analysis of the data to determine the volumetric flow rate of the gas from the voltage signal. Moreover, in one embodiment, the processor 212 may also be configured to display the determined volumetric flow rate of the gas on the display 216.

In another embodiment, if the flow rate of the gas does not entail formation of the vortices in the fluid conduit 222 (e.g., in the first flow regime), the DC voltage signal may be generated by the sensing element 211. Accordingly, the processor 212 may determine the magnitude ($V_{amp}$) of the DC voltage signal. In such an instance, the processor 212 may be configured to determine the mass flow rate of the gas based on the magnitude ($V_{amp}$) of the voltage signal. Further, the processor 212 may be configured to determine the volumetric flow rate of the gas based on the calibration function that was developed during the learning phase of the system 200. Moreover, in one embodiment, the processor 212 may also be configured to display the determined volumetric flow rate of the gas on the display 216.

Additionally, the system 200 may also include the condition detector 218. In one embodiment, the condition detector 218 may be disposed on or about the housing 202. The condition detector 218 may be configured to detect occurrence of one or more environmental conditions and/or gas leakage from the system 200. The one or more environmental conditions include, but are not limited to, an earthquake, fire, flood, snow storm, storm, or combinations thereof. In order to detect the environmental conditions and/or the gas leakage, the condition detector 218 may include one or more sensors that aid in the detection of the earthquake, fire, flood, snow storm, gas leakage, storm, or combinations thereof. Moreover, the tampering detector 220 may also be disposed on or about the housing 202 and configured to detect any tampering of the system 200.

In one embodiment, the condition detector 218 may be configured to communicate signals indicative of the detection of the environmental conditions and/or the gas leakage to the processor 212. Also, in one embodiment, the tampering detector 220 may be configured to communicate signals indicative of the tampering of the system 200 to the processor 212. Upon receipt of the one or more such signals from the condition detector 218 and/or the tampering detector 220, the processor 212 may be configured to operate the shut-off valve to stop the flow of the gas through the housing 202.

In the presently contemplated configuration depicted in FIG. 2, the flow conduit 222 is shown as being disposed within the flow sensor 210. However, in some embodiments, the flow conduit 222 may be in fluid communication between the input port 204 and the output port 206 inside the housing 202. Moreover, in certain embodiments, the gas analyzer 207, the flow manager 208, and/or the flow disrupter 209 may be disposed in the flow conduit 222. In such a configuration, the flow sensor 210 may include the sensing element 211 disposed in the by-pass channel 224.

As previously noted, in the first flow regime, no vortices are formed in the gas flowing in the housing 202 and the sensing element 211 of the flow sensor 210 may generate the DC voltage having the amplitude characteristics such as the magnitude ($V_{amp}$). Also, in the second flow regime, the vortices are formed in the gas flowing in the housing 202 and the sensing element 211 may generate the AC voltage signal having the temporal characteristics such as the frequency ($V_f$). In accordance with aspects of the present specification, the system 200 may be configured to perform self-diagnosis in case of malfunctioning of one or more components of the system 200. In one embodiment, the processor 212 may be employed to aid in the self-diagnosis of the system 200. In one embodiment, the processor 212 may be employed to identify the one or more malfunctioning components. By way of example, the processor 212 may be configured to diagnose that the flow sensor 210 is malfunctioning when flow is in the third or "intermediate" flow regime and the DC voltage from the sensor has significantly drifted from its calibrated value. In other example, malfunction may be symptomatic when the amplitude characteristics of the DC voltage are significantly measurable in the second flow regime and/or the temporal characteristics of the AC voltage signal are significantly measurable in the first flow regime. One possible reason for such a malfunctioning of the flow sensor 210 may be an accumulation of impurities on or around the sensing element 211. In accordance with aspects of the present specification, once the malfunctioning of the flow sensor 210 is identified, the processor 212 may be configured to update the calibration function, thereby recalibrating the system 200. Recalibrating the system 200 aids in compensating for the effect of the accumulation of impurities on or around the sensing element 211.

Implementing the system 200 for metering gas as described with respect to FIG. 1 aids in determining flow parameters such as the mass flow rate of the gas, the accumulated volume of the gas, the volumetric flow rate of the gas, the cumulative gas volume per the determined time unit, or combinations thereof. More particularly, flow parameters may be determined corresponding to different flow regimes. Moreover, the flow parameters thus determined may not be impacted by gas density fluctuations, moisture fluctuations, gas mixture fluctuations, and the like.

Figure 4B:
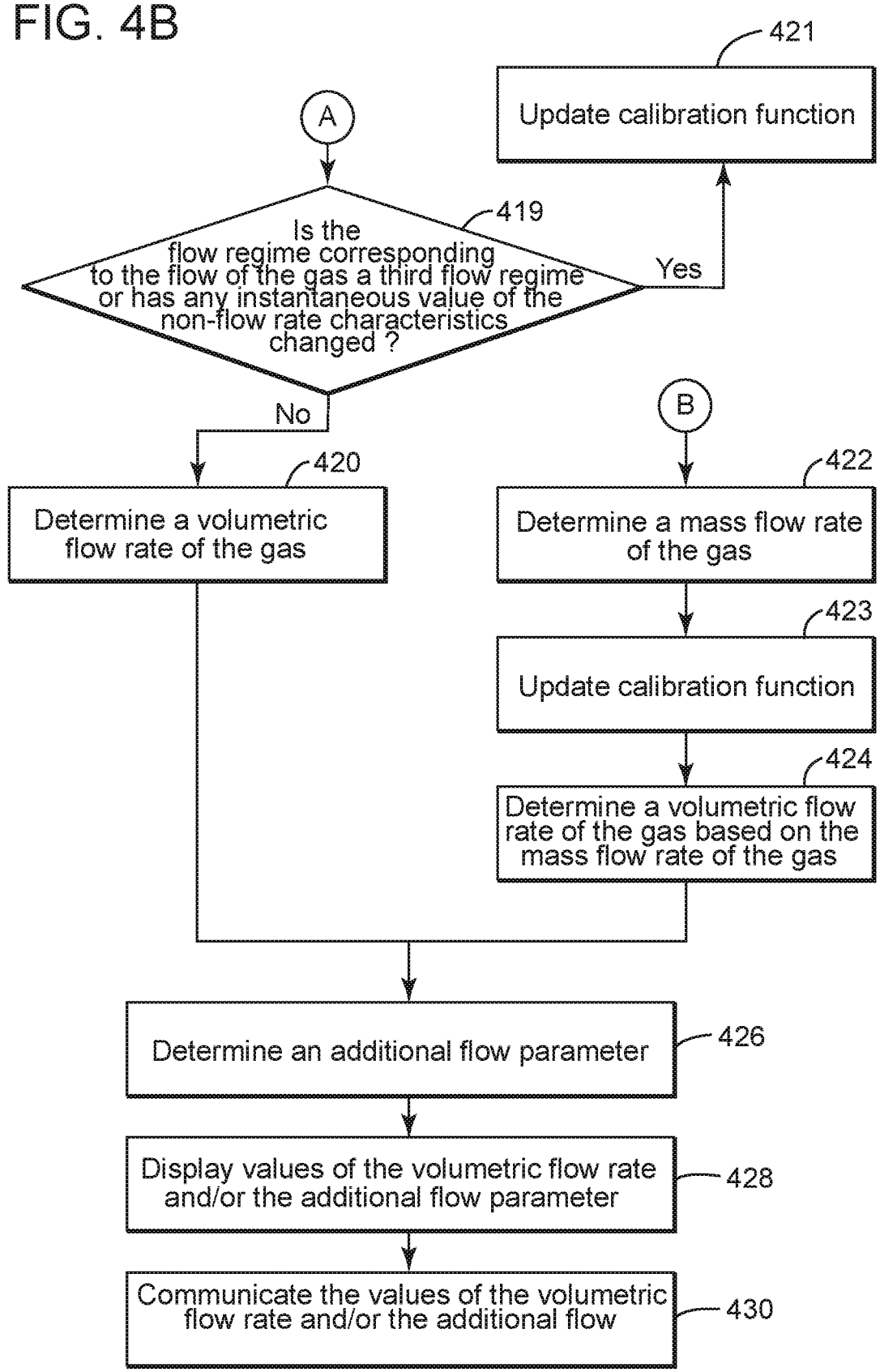

FIGS. 4A and 4B depict a flow chart 400 representative of an example method for metering gas, in accordance with aspects of the present specification. The method of FIGS. 4A and 4B is described in conjunction with the elements of FIG. 2. As noted previously, the system 200 includes the housing 202, the input port 204, the output port 206, the gas analyzer 207, the flow manager 208, and the flow sensor 210. The flow sensor 210 may include one or more of the flow conduit 222, the bypass channel 224, the flow disrupter 209, and the sensing element 211. The system 200 may further include the processor 212, display 216, condition detector 218, and tampering detector 220 disposed on or around the housing 202. In one example embodiment, the system 200 may be operatively coupled to the pipeline 214 and configured for metering the gas flowing through the pipeline 214.

In one embodiment, during a learning phase, the system 200 may be trained to develop a calibration function indicative of a relationship between a volumetric flow rate and a mass flow rate of the gas in a third flow regime. As previously noted, the third flow regime includes an overlap region of a first flow regime and a second flow regime. In another embodiment, the calibration function may be developed when the system 200 is operating to meter the gas. In yet another embodiment, the calibration function that is developed during the learning phase may be updated continuously or at regular intervals of time when the system 200 is operating to meter the gas.

Once the gas enters the system 200 through the input port 204, a portion of the gas may pass through the flow sensor 210. The gas from the housing 202 may exit from the output port 206.

As indicated by step 402, the system 200 may be configured to monitor one or more environmental conditions, gas leakage from the system 200 and/or tampering of the system 200. Some examples of the environmental conditions may include but, are not limited to, an earthquake, fire, flood, snow storm, storm, or combinations thereof. As noted previously, the one or more environmental conditions and/or the gas leakage may be monitored by the condition detector 218. The tampering of the system 200 may be monitored by the tampering detector 220.

Further, a check may be carried out at step 404 to determine occurrence of one or more of the environmental conditions, gas leakage from the system 200, and/or tampering of the system 200. In one embodiment, the condition detector 218 and/or the tampering detector 220 are configured to generate signals indicative of the occurrence of environmental conditions, gas leakage from the system 200, and/or tampering of the system 200. The processor 212 is configured to detect the occurrence of any of the environmental conditions, gas leakage from the system 200, and/or tampering of the system 200 based on the signals received from the condition detector 218 and/or the tampering detector 220. At step 404, if the occurrence of any of the environmental conditions, the gas leakage, or the tampering is determined, the system 200 may be shut down, as indicated by step 406. In another embodiment, the system 200 may be shut down in case of certain billing related issues. For example, the system 200 may be shut down if a customer fails to pay a bill within a prescribed duration. In order to shut down the system 200, in one embodiment, the processor 212 is configured to operate a shut-off valve located within the flow manager 208 to stop the flow of the gas through the flow conduit 222.

Although, the flow chart 400 of FIGS. 4A-4B depicts steps 402, 404, and 406 as being performed at the outset, it may be noted that steps 402-406 may be performed at any time during the process of metering the gas. In one embodiment, the environmental conditions, gas leakage, and tampering of the system 200 may be continuously monitored while the system 200 is in operation.

However, at step 404, if it is determined that the environmental conditions or the gas leakage did not occur and/or the system 200 has not been tampered with, at least one physical characteristic of the flow of the gas in the flow conduit 222 may be modified, as indicated by step 408. As will be appreciated, physical characteristics including, but not limited to, a separability of the flow of the gas, pressure of the gas, temperature of the gas, level of impurities in the gas, or combinations thereof may affect measurement results. Accordingly, it may be desirable to account for one or more of these physical characteristics while metering of the gas. Consequently, at least one physical characteristic of the flow of the gas is modified, as indicated by step 408. In one example, the at least one physical characteristic may be modified by the flow manager 208 under the control of the processor 212.

Subsequently, at step 410, one or more non-flow rate characteristics of the gas may be determined. In one embodiment, the one or more non-flow rate characteristics may be determined by the gas analyzer 207. Some examples of the non-flow rate characteristics may include but, are not limited to, a gas density, gas temperature, gas pressure, gas mixture, energy content of the gas, levels of various impurities contained in the gas, or combinations thereof. In one embodiment, when a flow disrupter such as the flow disrupter 209 is disposed within the gas analyzer 207, the flow disrupter 209 may also aid in the determination of non-flow rate characteristics.

In addition, at step 412, the flow of the gas in the housing 202 and/or flow conduit 222 may be disrupted by the flow disrupter 209. In one embodiment, at least some flow characteristics of the gas may be modified due to disturbances imparted by the flow disrupter 209 in the flow of the gas. For example, depending on the flow rate of the gas, vortices may be formed in the gas flowing in the flow conduit 222.

Also, an electrical signal may be generated by the flow sensor 210 in response to the flow characteristics of the gas in the housing 202, as indicated by step 414. In one embodiment, the sensing element 211 may be employed in the flow sensor 210 to generate the electrical signal. As noted previously, if no vortices are formed in the gas, a DC voltage signal may be generated by the sensing element 211. However, if the vortices are formed in the gas, an AC voltage signal may be generated by the sensing element 211. In certain embodiments, the AC voltage signal may also have a DC value. Amplitude characteristics and/or temporal characteristics of the voltage signal may be proportional or directly related to the flow rate of the gas flowing through the flow conduit 222. The electrical signal (e.g., the voltage signal) generated by the sensing element 211 may then be processed to determine a flow regime corresponding to the flow of the gas, as indicated by step 416. In one embodiment, the voltage signal may be processed by the processor 212 by performing spectral analysis of the electrical signal to determine the flow regime.

Accordingly, at step 418, a check may be carried out to determine whether the flow regime corresponding to the flow of the gas flowing through the system 200 is the first flow regime. In one embodiment, the processor 212 may be used to determine the flow regime corresponding to the flow of the gas flowing through the system 200.

In one embodiment, if a DC signal is received by the processor 212 from the flow sensor 210, the processor 212 may be configured to determine that the flow regime of the flow rate of the gas is the first flow regime. By way of example, if the frequency of the voltage signal received from the flow sensor 210 has a value of zero, the processor 212 may be configured to determine that the flow regime of the flow rate of the gas is the first flow regime. In another example, the processor 212 may be configured to determine that the flow regime of the flow rate of the gas is the first flow regime based on a DC voltage level of the voltage signal.

At step 418, if it is determined that the flow regime corresponding to the flow of the gas is the first flow regime, a mass flow rate may be determined based on the amplitude characteristics of the DC voltage signal, as indicated by step 422. In one embodiment, the mass flow rate of the gas is determined by the processor 212.

Moreover, at step 423, the calibration function is updated. The calibration function may be updated depending on the instantaneous values of the non-flow rate characteristics such as one or more of the constituents of the gas, temperature, pressure, and caloric value of the gas, and/or levels of various impurities contained in the gas. In one embodiment, for a first time use of the system 200, updating of the calibration function includes developing the calibration function.

Thereafter, at step 424, the volumetric flow rate of the gas may be determined by the processor 212 based on the mass flow rate of the gas determined at step 422. In another embodiment, the processor 212 may be configured to determine the volumetric flow rate of the gas by processing mass flow rate of the gas via the use of the calibration function determined during the learning phase or the updated calibration function determined at step 423. Control may be passed to step 426.

With returning reference to step 418, if an AC voltage signal is received by the processor 212 from the flow sensor 210, the processor 212 may be configured to determine that the flow regime corresponding to the flow of the gas is not the first flow regime. By way of example, if the frequency of the voltage signal has a non-zero value, the processor 212 may be configured to determine that the flow regime corresponding to the flow rate of the gas is not the first flow regime.

At step 418, if it is determined that the flow regime corresponding to the flow of the gas is not the first flow regime, an additional check may be carried out at step 419 to determine if the flow regime corresponding to the flow of the gas is the third flow regime or any instantaneous value of the non-flow rate characteristics has been changed. If it is determined that the flow regime corresponding to the flow of the gas is the third flow regime or any instantaneous value of the non-flow rate characteristics has been changed, the calibration function determined during the learning phase may be updated as indicated by step 421. The calibration function may be updated depending on the instantaneous values of the non-flow rate characteristics such as one or more of the constituents of the gas, temperature, pressure, and caloric value of the gas, and/or levels of various impurities contained in the gas. In one embodiment, for a first time use of the system 200, updating of the calibration function may include developing the calibration function.

However, at step 419, if it is determined that neither the flow regime corresponding to the flow of the gas is the third flow regime nor there has been any change in the instantaneous value of the non-flow rate characteristics, the processor 212 may be configured to determine that the flow regime corresponding to the flow rate of the gas is the second flow regime. Consequently, a volumetric flow rate of the gas may be determined based on the temporal characteristics of the AC voltage signal, as depicted by step 420. In one embodiment, the volumetric flow rate of the gas is determined by the processor 212. Control may be passed to step 426.

At step 426, an additional flow parameter may be determined. In one embodiment, the additional flow parameter such as an accumulated volume of the gas may be determined by the processor 212 based on the volumetric flow rate determined at either at step 420 or step 424. As noted previously, the calibration function has been developed and/or updated depending on the instantaneous values of the temperature and/or pressure of the gas in the housing 202. Consequently, as the volumetric flow rate and/or the additional flow parameter are determined after processing the mass flow rate of the gas via the updated calibration function, the determined values of the volumetric flow rate and/or the additional flow parameter may be representative of temperature and/or the pressure corrected values of the volumetric flow rate and/or the additional flow parameter.

Moreover, the determined values of volumetric flow rate and/or the additional flow parameter may be visualized on displays as indicated at step 428. In one embodiment, the processor 212 is configured to display the volumetric flow rate and/or the additional flow parameter on the display 216.

Additionally, in certain embodiments, the values of the volumetric flow rate and/or the additional flow parameter may be communicated to a remote location as indicated by step 430. In some embodiments, the values of the volumetric flow rate and/or the additional flow parameter may be communicated to one or more displays disposed at a remote location. In one embodiment, the processor 212 may be configured to communicate the values of the volumetric flow rate and/or the additional flow parameter to the one or more remotely located displays over a wireless communication.

In certain embodiments, the determined values of the volumetric flow rate and the additional flow parameters such as the accumulated volume of the gas may be used to bill respective customer. More particularly, a bill amount may be determined based on the accumulated volume of the gas.

Any of the foregoing steps and/or system elements may be suitably replaced, reordered, or removed, and additional steps and/or system elements may be inserted, depending on the needs of a particular application, and that the systems of the foregoing embodiments may be implemented using a wide variety of suitable processes and system elements and are not limited to any particular computer hardware, software, middleware, firmware, microcode, etc.

The system and method for metering gas described hereinabove greatly improves the accuracy of measurement of the flow parameters of the gas such as the volumetric flow rate of the gas. Use of the non-flow rate characteristics of the gas in developing the calibration function aids in enhancing the accuracy of the measurement of the flow parameters. Moreover, the flow manager aids in maintaining one or more physical characteristics of the flow of the gas within corresponding desired limits thereby minimizing the effect of the physical characteristics on the accuracy of the measurement of the flow parameters. Also, the system facilitates a hazard free setup as the system is configured to stop the flow of the gas on detection of occurrence of an earthquake, fire, flood, snow, gas leakage, tsunami, or tampering of the system. Additionally, use of electronic sensing elements leads to increased mass production and reduces overall cost of manufacturing of such gas metering systems.

Furthermore, the system is also capable of performing self-diagnosis in case of malfunctioning of one or more components of the system. Also, the automated recalibration of the system aids in mitigating the influence of the impurities in the gas on the measurements performed by the system. Consequently, the accuracy of the measurements may be maintained for the lifetime and operation of the system. In addition, the measurement of the volumetric flow rate based on the vortices is impervious to any impurities in the gas.

The foregoing examples, demonstrations, and method steps such as those that may be performed by the system may be implemented by suitable code on a processor-based system, such as a general-purpose or special-purpose computer. Different implementations of the systems and methods may perform some or all of the steps described herein in different orders, parallel, or substantially concurrently. Furthermore, the functions may be implemented in a variety of programming languages, including but not limited to C++ or Java. Such code may be stored or adapted for storage on one or more tangible, computer readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

The discussion continues below to describe additional features for the electronic flow meters contemplated herein. These features are useful to characterize flow of fuel gas for use in customer billing applications, but the concepts may find use in other applications as well. A proposed design employs a sensor that can capture data that defines measured flow conditions (e.g., pressure, temperature, etc.) for a sample of fuel gas. This feature permits the device to calculate the volume of gas flowing through the meter more accurately and to account for real-time or contemporaneous conditions of the flowing fuel gas. And, by leveraging semiconductor-based manufacturing techniques, the design may provide a robust, low cost device in compliance with legal metrology standards as an alternative to mechanically-based flow meters.

Figure 5:
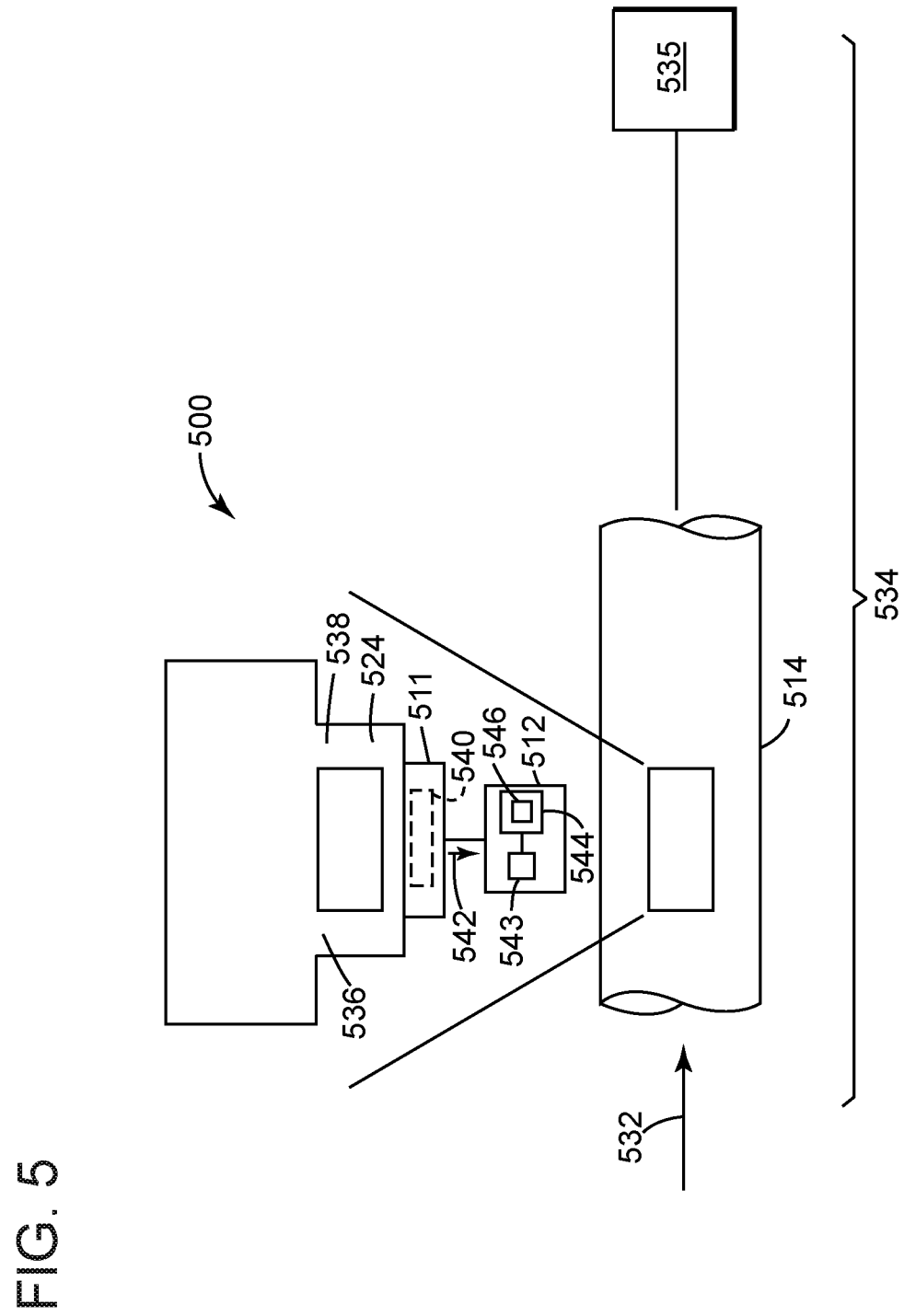
FIG. 5 depicts a schematic diagram of an exemplary embodiment of a system that can quantify volumetric flow of fuel gas.

FIG. 5 depicts, schematically, an exemplary embodiment of a flow metering system 500. This embodiment is shown to couple with the pipeline 514 that carries material 532. The pipeline 514 may integrate as part of a distribution network 534 that delivers material 532 to a customer 535. Material 532 may be a gas, a liquid, a particulate solid, or a liquid/solid mix. In one example, used throughout, material 532 is fuel gas (e.g., natural gas). The flow metering system 500 may be useful to quantify volumetric flow of the fuel gas for purposes of billing the customer 535. The by-pass channel 524 may have open ends (e.g., a first open end 536 and a second open end 538) to direct part of the flow, or a "sample" or a "stream," in proximity of the sensing element 511 and then return the sample back to the flow conduit 522 (also, "pass-through channel 522"). As shown, the sensing element 511 may have circuitry 540 that generates a signal 542 that reflects one or more characteristics of the flow stream or material 532, generally. The circuitry 540 may couple with the processor 512, showing here with computing components, for example, a processor 543 that couples with memory 544 having executable instructions 546 stored thereon. The computing components may operate to process the signal 542, for example, to quantify volumetric flow of material 532 in the pipeline 514. The volumetric flow nominally reflects demand by the customer 535 to generate appropriate billing services.

As noted throughout, the system 500 can be configured to characterize flow in a way to improve values for volumetric flow that result from the processor 512. These configurations may employ circuitry 540 so that the signal 542 provides data that reflects measured conditions (like pressure and temperature) of the stream of the material 532 at or proximate the sensing element 511. The data may also reflect other flow characteristics, as well. Data for measured pressure is important at low flow conditions for the processor 512 to more accurately account for density of the material 532 in or proximate (or very close to) the by-pass channel 524. Across all flow conditions, the processor 512 can use data for the reference conditions, typically assigned by legal metrological standard, to "adjust" values for volumetric flow to values that provide accurate and reliable metrics for billing consumers. In turn, the system 500 may find wide use and adoption for metering fuel gas in both residential applications (low pressure) and commercial applications (high pressure).

Practices-to-date predominantly assume that fuel gas remains at constant pressure set by a pressure regulator upstream of (and spaced apart from) the device. By measuring pressure data, however, the system 500 may reduce the likelihood that potential human errors can percolate into values for volumetric flow or for volumetric flow that is "corrected" (to reference conditions). These errors may arise from deficiencies in the pressure regulator, for example, due to manufacture or from cases in which an end user (e.g., technician) improperly installs or sets-up the pressure regulator found in proximity to the device.

Figure 6:
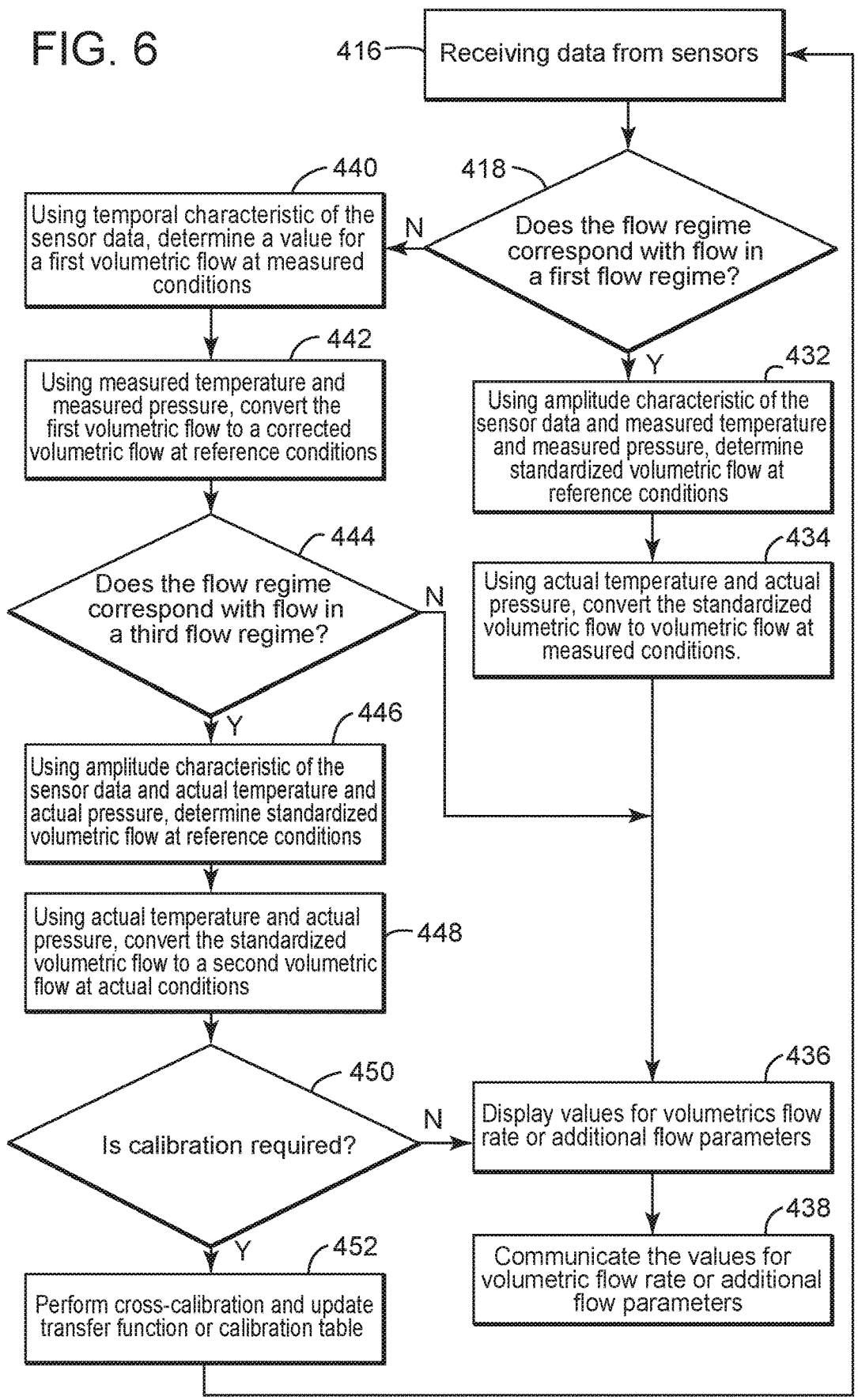
FIG. 6 depicts a flow diagram of an exemplary embodiment of a method of operating the flow meter of FIG. 5.

FIG. 6 depicts a flow diagram of an exemplary embodiment of the method 400 to improve accuracy of the system 500. This diagram outlines stages that may embody executable instructions 546 for one or more computer-implemented methods and/or programs. The executable instruction 546 may be stored on the memory 544 as firmware or software. The processor 543 may have access to the memory 544 so that, when the processor 542 executes the executable instructions 546, the processor 543 is configured for certain functions, one or more of which may be represented by the stages of the method 400. These stages can be altered, combined, omitted, and/or rearranged in some embodiments.

Operation of the method 400 may generate values that correspond with volumetric flow of the "main" stream in the pass-through channel 522. The method 400 may include, at stage 416, processing the incoming sensor data and, at stage 418, assessing whether the flow regime corresponds with a first flow regime, for example, "low" flow conditions that prevail in the main stream. If affirmative, the method 400 may continue, at stage 432, using amplitude characteristics of the incoming sensor data and values for measured temperature and measured pressure to determine standardized volumetric flow at reference conditions. The method 400 may also include, at stage 434, using values for measured temperature and measured pressure to convert the standardized volumetric flow to volumetric flow at the measured conditions. The method 400 may further include, at stage 436, displaying values for parameters of flow and, at stage 438, communicating the values. In one implementation, the method 400 may continue, at stage 416, to monitor or sample the incoming sensor data. When "low" flow conditions do not prevail in the main stream, the method 400 may include, at stage 440, using temporal characteristics of the incoming sensor data to determine a first volumetric flow of the main stream at the measured conditions. The method 400 may also include, at stage 442, using values for measured temperature and measured pressure to convert the first volumetric flow to a "corrected" volumetric flow that describes volumetric flow at reference conditions. The method 400 may further include, at stage 444, assessing whether the flow regime corresponds with a second flow regime, for example, "high" flow conditions of the main stream. If affirmative, the method 400 may continue to stage 436, 438 to display and communicate values for the flow parameters (e.g., volumetric flow). The method 400 may, alternatively, assume that flow regime corresponds with "intermediate" flow conditions and continue, at stage 446, using amplitude characteristics of the incoming sensor data and values for the measured temperature and measured pressure to determine the standardized volumetric flow at reference conditions. The method 400 may also include, at stage 448, using values for the measured temperature and the measured pressure to convert the standardized volumetric flow to a second volumetric flow at the measured conditions. The method 400 may further include, at stage 450, determining whether calibration is required. If so, the method 400 may include at stage 452, performing cross-calibration and updating the transfer function or calibration table. In one implementation, the method 400 may continue, at stage 416, to continue monitoring or sampling of the incoming sensor data.

At stage 418, the method 400 may identify the condition of the main stream as the "low" flow condition. The method 400 may include stages to determine that the flow of the main stream is laminar, which is characteristic of "low" flow. These stages may compare measured flow parameters, as defined by the sensor data, to some threshold value, like a maximum voltage value that is known to indicate the transition in the main stream from laminar flow to turbulent flow. With reference also to FIG. 3, the first data curve 306 is consistent with the voltage response at "low" flow conditions (or first flow condition or the first flow regime). This response may correspond to DC voltage, where the amplitude characteristic (or amplitude Vamp) remains relatively steady at value because vortices do not form in the main stream at these low flow conditions to induce disturbances in the signal 542.

At stages 432, 434, the method 400 uses the amplitude characteristics of the sensor data to determine the volumetric flow for low flow conditions of the main stream. Generally, volumetric flow may be based on a mass flow sensing mechanism. Here, the method 400 may include one or more stages for analyzing the incoming sensor data to arrive at the volumetric flow. These stages may result in the first volumetric flow (at stage 432), which may be "standardized" or "corrected" to some pre-determined or assigned reference conditions of temperature and pressure. For example, in the United States, reference conditions define values for pressure (14.72 psi) and 60° F. The resulting "standardized" volumetric flow is often measured in standard liter per minute (SLPM) or similar units of measure. Transfer functions and similar signal or data processing techniques may be useful for this purpose. In one implementation, the stages may access a calibration table and select an entry from the calibration table for the "standardized" volumetric flow. This entry may correspond with the amplitude characteristic of the incoming sensor data. Examples of the calibration table may include entries with data that associate the amplitude with volumetric flow rate at reference conditions (e.g., reference pressure and reference temperature). This feature is beneficial for a given amplitude (Ai) or a given amplitude range to correspond with a value (Vi) for the volumetric flow rate. Table 1 below shows an example of a calibration table.

TABLE 1

| Entry | Amplitude (mV) | Volumetric flow (gal/s) |
| --- | --- | --- |
| 1 | A1 | V1 |
| 2 | A2 | V2 |
| 3 | A3 | V3 |
| 4 | A4 | V4 |

At stage 434, the method 400 may convert the first volumetric flow to the second volumetric flow. The second volumetric flow may have a value that reflects measured conditions (for example, measured temperature and measured pressure) proximate the sensor. This value may be measured in actual liters per minute (ALPM) or similar units of measure. To arrive at this value, the method 400 may include states to calculate the value using the Ideal Gas Law, as illustrated in Equation (2) below:

$$PV = nRT,  \qquad \text{Equation (2)}$$

Where P is the measured pressure, T is the measured temperature, R is the specific gas constant, and n is the number of molecules of the gas (or the number of moles of the material).

At stages 436, 438, the method 400 generates the output that reflects the volumetric flow rate. These stages may include one or more stages for providing some visual representation of the appropriate values, for example, on a display or screen. Other functionality may convey the volumetric flow rate to a remote processing device (e.g., network, network computer, etc.) for purpose of storage or processing, as desired.

At stage 440, 442 the method 400 uses temporal characteristics of the incoming sensor data to determine the volumetric flow for the main stream. The method 400 may adjust or "correct" the volumetric flow to the "corrected" volumetric flow at reference conditions. As noted above, values for the references conditions are assigned by standard or specification. The calculation can apply the Ideal Gas Law, noted as Equation (1) above, and recited below as Equation (3):

$$V_r = \left(\frac{P_m}{P_r}\right) \times \left(\frac{T_r}{T_m}\right) \times V_m, \quad \text{Equation (3)}$$

where $V_r$ is volumetric flow at reference conditions, $V_m$ is volumetric flow at measured conditions, $P_m$ is the measured pressure (as measured by the sensor 511), $P_r$ is the reference pressure, $T_m$ is the measured temperature (as measure by the sensor 511), and $T_r$ is the reference temperature. In some implementations, the method 400 may include stages to access another table that stores data that reflects references conditions ($P_r$, $T_r$) wherein the entries correspond with values for different countries, different standards, or other delineations among these values.

At stage 444, the method 400 may identify the condition of the main stream as the "high" flow condition or the "intermediate" flow condition. The method 400 may include stages, for example, to determine that the flow of the main stream is turbulent. These stages may compare measured flow parameters, like from the sensor data, to some threshold value, like a minimum voltage value that is known to indicate the transition in the main stream from laminar flow to turbulent flow. With reference to FIG. 3, the second data curve 308 is consistent with the voltage response for "high" flow conditions (or second flow condition or second flow regime). This response may correspond to AC voltage, or like oscillating signal, where the temporal characteristic (or frequency Vf) fluctuates because the turbulent condition of the main stream forms vortices that induce disturbances in the signal 542. "High" flow conditions trigger the method 400 to display or generate the necessary output for volumetric flow determined using the temporal characteristics (at stages 440, 442). In one implementation, the method 400 may also include stages to determine whether the measured parameters indicate intermediate flow conditions. The threshold value may correspond with a range of voltage values. With reference to FIG. 3, the third data curve 310 is consistent with this range of voltage responses that make up an overlap region that includes parts of the data curves 306, 308. This overlap region corresponds with measurements of both temporal characteristics and amplitude characteristic of the main stream (for example, because vortices are present in the main stream).

At stages 446, 448, the method 400 may determine the volumetric flow of the main stream. These stages may include stages discussed above (in connection with stage 432). For example, the stages may use the amplitude characteristics of the incoming sensor data and the measured temperature and the measured pressure (from the sensor) to determine the first volumetric flow at reference conditions and convert the first volumetric flow to the second volumetric flow.

At stage 450, the method 400 may determine whether to perform cross-calibration. In one implementation, the method 400 may include stages for comparing values for volumetric flow based on temporal characteristics of the incoming data (at stage 440) and based on the amplitude characteristics of the incoming data (at stage 448) and for assigning a relationship that defines the relative position of the first volumetric flow to the second volumetric flow. The relationship may inform the accuracy of volumetric flow (at stages 432, 434, 446, 448). When small or insignificant (e.g., <approximately 1%), the relationship indicates that the previously-determined values accurately reflect the values for volumetric flow in the main stream.

At stage 452, the method 400 may perform cross-calibration in response to the relationship. Cross-calibration may be required, for example, when the relationship between the first volumetric flow and the second volumetric flow is large (e.g., >approximately 1%). In some examples, the relationship may reflect other changes in the non-flow rate parameters (e.g., gas density) that prevail in the system. This stage may, in turn, update variables in the transfer function, an example of which may include Fast Fourier Transform (FFT), or update or change values found in the calibration table. Practical approaches may entail any one of (i) scaling the calibration curve based on the ration of actual DC reading to default values for the sensor, (ii) baseline shifting to the calibration curve based on the difference between the actual DC reading and the default value, (iii) re-calculating of the calibration curve based on multiple data points spanning over the overlap region, or (iv) selecting or re-calculating of a new calibration curve from a group of curves in memory based on a numerical relationship between the actual DC reading and a range of expected DC values.

Figure 7:
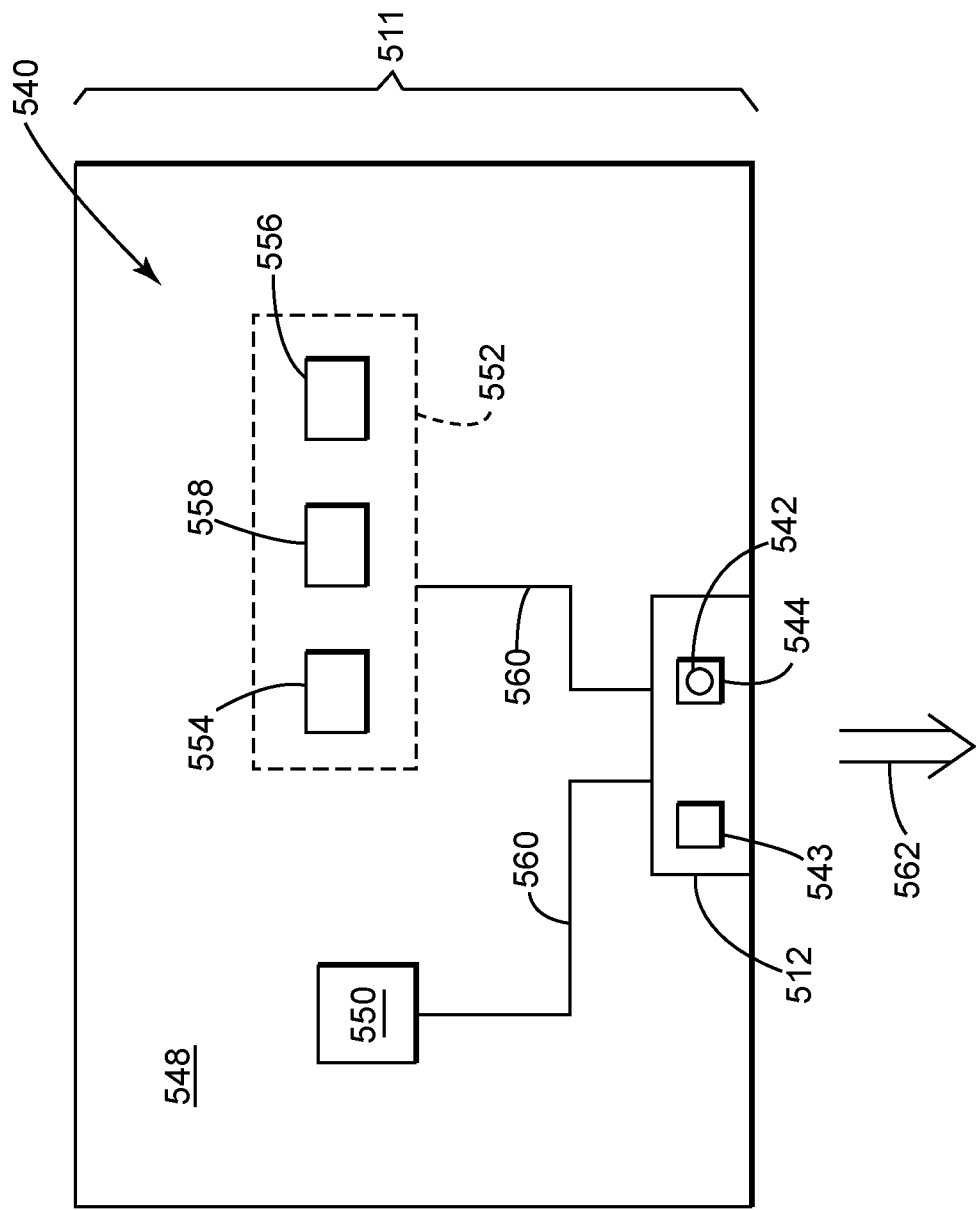
FIG. 7 depicts a flow diagram of an example of the method of FIG. 6.

Referring now to FIG. 7, the discussion turns to exemplary structure for the sensing element 511 to provide data for the system 500 to calculate volumetric flow and to correct for ambient conditions. This structure may embody micro-electromechanical (MEMS) structure or comparable semiconductor-based packages, chip-on-chip, and like solid-state constructs, any one of which may be small and easy (and economical) to manufacture at scale. The embodiments may include a substrate 548 that supports the circuitry 540, which may form integrated circuits that integrate into or onto the substrate 548. Exemplary integrated circuits may include one or more parameter probes (e.g., a pressure probe 550 and a temperature probe 552). It may be helpful that the temperature probe 552 includes a pair of temperature-sensitive devices 554, 556, which may be spaced apart from one another on either side of a heating element 558. The substrate 548 may include a buss structure 558 that couples the probes 550, 552 with the processor 512. The buss structure 560 may be configured to exchange signals (e.g., the signal 542) between the coupled devices. These components of the processor 512 may integrate onto the substrate 548 or reside separately, as desired. The executable instructions 546 may configure the processor 512 to perform functions or exhibit capabilities including, for example, processing the signal 542 to generate an output 562, for example, that transmits the value for volumetric flow of material 532 through the pipeline 514.

The sensing element 511 may embody structure that conforms to desired form factors to compliment use of system 500. The substrate 548 may embody silicon or ceramic material, although printed circuit board (PCB) may also suffice. The probes 550, 552 may form integrally as part of the substrate material, as if manufactured using techniques to build integrated circuitry onto a silicon wafer or as part of a ceramic device, for example. Other techniques may allow the probes 550, 552 to be disposed in a manner that makes appropriate electrical contacts with the buss structure 558 on the substrate 548.

The probes 550, 552 may be configured to respond to parameters of flowing material 532 in the by-pass channel 524. These configurations may have features that accord with MEMS packages and devices. The features may result in device sizes that are less than 1 mm. For sensing, the devices may employ piezoelectric, piezoresistive, capacitive, or inductive technologies, but other technologies may develop after the time of this writing that will work in this concept as well. Temperature sensing may require use of thermocouples or thermisters as the temperature sensitive devices 550, 552.

Figure 8:
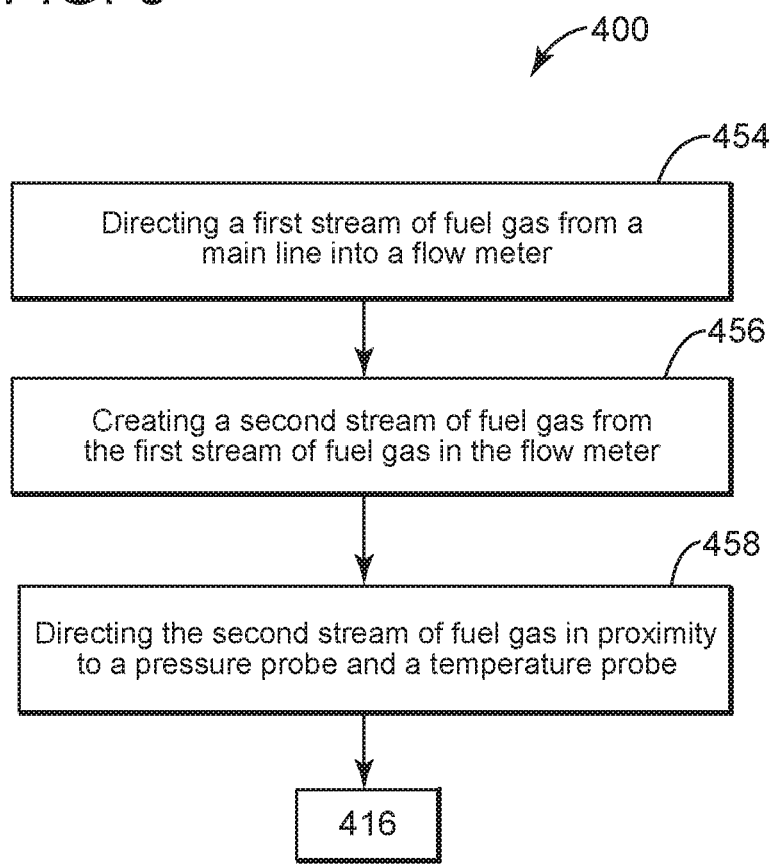
FIG. 8 depicts a schematic diagram of an example of a sensor for use on the flow meter of FIG. 5.

FIG. 8 depicts a flow diagram of an example of the method 400 with additional details of possible operation of the system 500. The method 400 may include, at stage 440, directing a first stream of fuel gas from a mainline into a flow meter and, at stage 442, creating a second stream of fuel gas from the first stream of fuel gas in the flow meter. The method 400 may also include, at stage 444, directing the second stream of fuel gas in proximity to a pressure probe and a temperature probe. The method 400 may continue, at stage 414, to generate a signal that reflects the localized pressure and localized temperature of the second stream of fuel gas.

At stage 440, the method 400 directs fuel gas from the mainline into the system 500. This stage creates a "measured" stream that, in effect, exhibits parameters representative of the flow of material 532 in the pipeline 514. In this regard, this stage may coincide with stages to install the system 500 in a location on the pipeline 514. This location may be in-line with the pipeline 514, for example, if the system 100 has flanged ends that can attach to corresponding pipe flanges on the pipeline 514. Alternatively, the location may reside outside of the pipeline 514. This location may cause the system 500 to attach to at its ends to openings in the pipeline 514 that permit flow of fuel gas to enter and exit the pass-through channel 522, but return to the pipeline 514.

At stage 442, the method 400 creates the second stream of fuel gas. This second stream may operate as a "sample" stream that flows through the by-pass channel 524. The sample stream may be "smaller" than the measured stream, but still exhibit parameters that permit use of data from the sample stream for purposes of calculating volumetric flow in the main line. In one implementation, the system 500 may be configured to condition the measured stream or the sample stream, often upstream of the first open end 536 of the by-pass channel 524. Such configurations may ensure that the flow of the sample stream has appropriate characteristics (e.g., turbulent flow, laminar flow, etc.) for purposes of generating data about the flow parameters, as noted herein.

At stage 444, the method 400 directs the second stream in proximity to probes. The by-pass channel 116 may be configured to expose the probes 550, 552 to the sample stream. These configurations may include apertures in the substrate 548 or like physical or mechanical designs. The apertures can cooperate with the design of probes 550, 552. In one implementation, this stage may include one or more stages for heating the sample stream, often as the sample stream transits the by-pass channel 524. Examples may include heating the sample stream at a location disposed between the temperature sensitive devices 550, 552. Stages may be required, for example, to activate the heating element 558 for this purpose.

In light of the foregoing, the improvements here enhance electronic meters with capabilities to meet legal metrology standards. These capabilities derive, at least in part, to use of pressure probes that can interrogate pressure of the sample stream. This feature allows the flow meter to more accurately calculate volumetric flow from mass flow and to correct for ambient condition.

This written description uses examples to disclose the invention, including the best mode, and also to enable any person skilled in the art to practice the invention, including making and using any devices or systems and performing any incorporated methods. An element or function recited in the singular and proceeded with the word "a" or "an" should be understood as not excluding plural said elements or functions, unless such exclusion is explicitly recited. References to "one embodiment" of the claimed invention should not be interpreted as excluding the existence of additional embodiments that also incorporate the recited features. Furthermore, the claims are but some examples that define the patentable scope of the invention. This scope may include and contemplate other examples that occur to those skilled in the art. Such other examples are intended to be within the scope of the claims if they have structural elements that do not differ from the literal language of the claims, or if they include equivalent structural elements with insubstantial differences from the literal language of the claims.

Examples appear below that include certain elements or clauses one or more of which may be combined with other elements and clauses describe embodiments contemplated within the scope and spirit of this disclosure.

What is claimed is:

1. An apparatus, comprising:
   a body having a pass-through channel forming a main fluid stream and at least one by-pass channel coupled with the pass-through channel;
   a semiconductor device comprising a sensor disposed proximate the at least one by-pass channel, the sensor configured to generate data that reflects measured conditions comprising at least one value for pressure and at least one value for temperature of a portion of the main fluid stream in the at least one by-pass channel; and
   a processing component coupled with the sensor to receive the data, the processing component comprising a processor, memory coupled with the processor, and executable instructions stored on the memory and accessible by the processor, the executable instructions comprising instructions that, when executed by the processor, configure the processor for:
   using one or both of amplitude characteristics of the data and temporal characteristics of the data to identify a flow regime for the main fluid stream and flow parameters thereof;
   selecting a process to determine a volumetric flow rate of the main stream in response to the flow regime;
   using data for the at least one value for pressure and the at least one value for temperature in the process to generate a value that defines the volumetric flow rate of the main stream; and
   generating an output with data that reflects the value for a reported volumetric flow rate of the main stream.

2. The apparatus of claim 1, wherein the process includes:
   using the at least one value for measured temperature and the at least one value for measured pressure to convert the amplitude characteristics of the data and the flow parameters to volumetric flow at the measured conditions of the main stream, wherein the value for the reported volumetric flow rate corresponds to the volumetric flow at the measured conditions or the standardized volumetric flow.

3. The apparatus of claim 2, wherein the flow regime corresponds with low flow conditions in the main stream.

4. The apparatus of claim 1, wherein the process includes,
using at least one value for measured temperature and the at least one value for measured pressure to convert the temporal characteristics of the data and the flow parameters to volumetric flow at the measured conditions of the main stream,
wherein the value for the reported volumetric flow rate corresponds to one of the volumetric flow at the measured conditions or the standardized volumetric flow.

5. The apparatus of claim 4, wherein the flow regime corresponds with high flow conditions in the main stream.

6. The apparatus of claim 1, wherein the process includes,
using the temporal characteristics and the flow parameters to determine a first volumetric flow at the measured conditions of the main stream;
using the amplitude characteristics to determine the flow parameters of the flow of the main stream from a calibration table;
using the at least one value for measured temperature and the at least one value for measured pressure to convert the flow parameters to a second volumetric flow at the measured conditions of the main stream,
comparing the first volumetric flow to the second volumetric flow;
assigning a relationship that defines the relative position of first volumetric flow to the second volumetric flow; and
performing cross-calibration to update the calibration table in response to the relationship identifying the flow regime having both temporal characteristics of the data and amplitude characteristics of the data,
wherein the value for reported volumetric flow rate corresponds with one of the first volumetric flow, the second volumetric flow, a first standardized volumetric flow, or a second standardized volumetric flow.

7. The apparatus of claim 6, wherein the flow regime at cross-calibration corresponds with intermediate flow conditions in the main stream.

8. The apparatus of claim 1, wherein the process includes:
using the temporal characteristics to determine a first volumetric flow at the measured conditions of the main stream;
using the amplitude characteristics and a transfer function to determine flow parameters of the main stream;
using the at least one value for measured temperature and the at least one value for measured pressure to convert the data and the flow parameters to a second volumetric flow at the measured conditions of the main stream,
comparing the first volumetric flow to the second volumetric flow;
assigning a relationship that defines the relative position of first volumetric flow to the second volumetric flow; and
performing cross-calibration to update the transfer function in response to the relationship identifying the flow regime having both temporal characteristics of the data and amplitude characteristics of the data,
wherein the value for the reported volumetric flow rate corresponds with one of first volumetric flow or second volumetric flow.

9. The apparatus of claim 1, further comprising:
a flow modifier disposed in the main stream, proximate the at least one by-pass channel and configured to modify at least one physical characteristic of the stream in the by-pass channel.

10. A method, comprising:
receiving a first stream of fuel gas;
separating a second stream from the first stream;
flowing the second stream in proximity to a sensor, the sensor providing data that reflects measured temperature and measured pressure of the second stream;
using one or both of amplitude characteristics of the data and temporal characteristics of the data to identify a flow regime for the first stream and flow parameters thereof;
selecting a process to determine a volumetric flow rate of the first stream in response to the flow regime;
using data for measured pressure and measured temperature in the process to generate a value that defines the volumetric flow rate of the first stream; and
generating an output with data that reflects the a value for a reported volumetric flow rate of the main stream.

11. The method of claim 10, wherein the process includes:
using the at least one value for measured temperature and the at least one value for measured pressure to convert the amplitude characteristics of the data to volumetric flow at the measured conditions of the first stream,
wherein the value for the reported volumetric flow rate corresponds to the volumetric flow at the measured conditions.

12. The method of claim 11, wherein the flow regime corresponds with low flow conditions in the first stream.

13. The method of claim 10, wherein the process includes,
using at least one value for measured temperature and the at least one value for measured pressure to convert the temporal characteristics of the data and the flow parameters to volumetric flow at measured conditions of the first stream,
wherein the value for the reported volumetric flow rate corresponds to one of the volumetric flow at the measured conditions or the standardized volumetric flow.

14. The method of claim 13, wherein the flow regime corresponds with high flow conditions in the main stream.

15. The method of claim 10, wherein the process includes,
using the temporal characteristics and the flow parameters to determine a first volumetric flow at the measured conditions of the main stream;
using the amplitude characteristics to determine the flow parameters of the first stream from a calibration table;
using the at least one value for measured temperature and the at least one value for measured pressure to convert the flow parameters to a second volumetric flow at the measured conditions of the main stream,
comparing the first volumetric flow to the second volumetric flow;
assigning a relationship that defines the relative position of first volumetric flow to the second volumetric flow; and
performing cross-calibration to update the calibration table in response to the relationship identifying the flow regime having both temporal characteristics of the data and amplitude characteristics of the data,
wherein the value for reported volumetric flow rate corresponds with one of first volumetric flow or second volumetric flow.

16. The method of claim 15, wherein the flow regime at cross-calibration corresponds with intermediate flow conditions in the main stream.

17. The method of claim 10, wherein the process includes:
using the temporal characteristics to determine a first volumetric flow at the measured conditions of the main stream;
using the amplitude characteristics and a transfer function to determine flow parameters of the first stream;
using the at least one value for measured temperature and the at least one value for measured pressure to convert the data and the flow parameters to a second volumetric flow at the measured conditions of the main stream,
comparing the first volumetric flow to the second volumetric flow;
assigning a relationship that defines the relative position of first volumetric flow to the second volumetric flow; and
performing cross-calibration to update the transfer function in response to the relationship identifying the flow regime having both temporal characteristics of the data and amplitude characteristics of the data,
wherein the value for the reported volumetric flow rate corresponds with one of first volumetric flow or second volumetric flow.

18. The method of claim 10, further comprising:
modifying flow of the first stream to induce vortices before separating the second stream.

19. The method of claim 10, further comprising:
modifying at least one physical characteristic of the second stream.

20. The method of claim 10, further comprising:
using a flow modifier in the first stream, modifying at least one physical characteristic of the second stream.

* * * * *